United States Patent
Bernardon

Patent Number: 5,786,379
Date of Patent: Jul. 28, 1998

[54] ADAMANTYL-SUBSTITUTED BIAROMATIC COMPOUNDS AND PHARMACEUTICAL/COSMETIC COMPOSITIONS COMPRISED THEREOF

[75] Inventor: Jean-Michel Bernardon, Le Rouret, France

[73] Assignee: Centre International de Recherches Dermatologiques Galderma, Valbonne, France

[21] Appl. No.: 759,312

[22] Filed: Dec. 2, 1996

[30] Foreign Application Priority Data

Dec. 1, 1995 [FR] France ................... 95 14260

[51] Int. Cl.$^6$ .............. A61K 31/38; A61K 31/335; A61K 31/235; A61K 31/19
[52] U.S. Cl. .............. 514/448; 514/447; 514/445; 514/568; 514/617; 514/467; 514/544; 514/712; 514/730; 514/685; 514/599; 514/355; 514/345; 514/472; 514/473; 514/541; 514/556; 549/71; 549/62; 549/68; 549/78; 549/479; 549/480; 549/483; 549/484; 560/59; 560/102; 560/257
[58] Field of Search ................... 560/159, 102, 560/257; 514/544, 513, 568, 717, 627, 617, 599, 685, 712, 730, 350, 351, 345, 354, 445, 447, 448, 472, 473, 541, 556, 557, 562; 562/492; 568/631, 331, 41, 42, 807; 564/171, 161, 74; 546/290, 298, 301, 312, 313; 549/64, 65, 66, 71, 69, 479, 480, 483, 497; 548/423, 424, 426, 427, 428

[56] References Cited

U.S. PATENT DOCUMENTS

| | | | |
|---|---|---|---|
| 4,925,658 | 5/1990 | Shroot et al. | 424/70 |
| 5,439,925 | 8/1995 | Bernardon et al. | 514/353 |
| 5,466,861 | 11/1995 | Dawson et al. | 560/100 |
| 5,498,795 | 3/1996 | Song et al. | 562/474 |
| 5,574,036 | 11/1996 | Bernardon et al. | 514/239.2 |
| 5,597,839 | 1/1997 | Bernardon et al. | 514/357 |

FOREIGN PATENT DOCUMENTS

| | | |
|---|---|---|
| 0232199 | 8/1987 | European Pat. Off. . |
| 0325540 | 7/1989 | European Pat. Off. . |
| 0409728 | 1/1991 | European Pat. Off. . |
| 0409729 | 1/1991 | European Pat. Off. . |
| 0679631 | 11/1995 | European Pat. Off. . |
| 2601002 | 1/1988 | France . |

OTHER PUBLICATIONS

Sarges, Reinhard et al., "Prep. of Retinoids and Their Use in Treating Skin Diseases and Leukemia", CA 119:95346, (1993).

Klaus, Michael et al., "Aromatic Carboxylic Acid Esters for use as Selective Retinoic Acid. Gamma. Receptor Ligands", CA127:50545 (1997).

Margnan, Jean et al., "Preparation of Aromatic Carboxylic Acids and their Derivatives for use in Cosmetics and Pharmaceuticals", CA 108:111 954 (1987).

*Primary Examiner*—Deborah Lambkin
*Attorney, Agent, or Firm*—Burns, Doane, Swecker & Mathis, L.L.P.

[57] ABSTRACT

Novel pharmaceutically/cosmetically-active adamantyl-substituted biaromatic compounds have the structural formula (I):

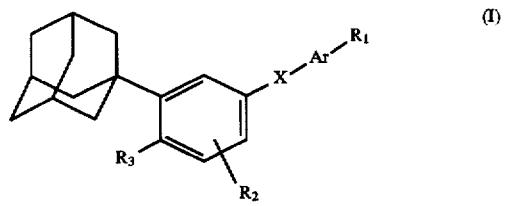

wherein Ar is a radical having one of the formulae (a')–(f'):

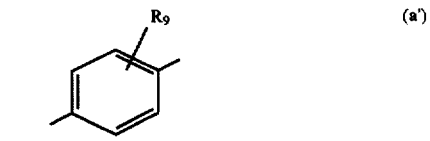

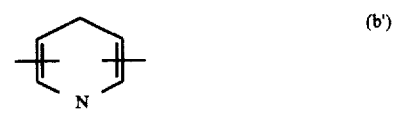

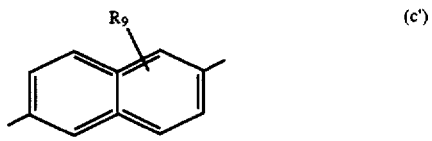

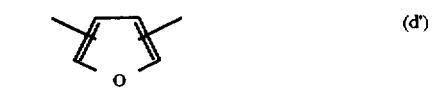

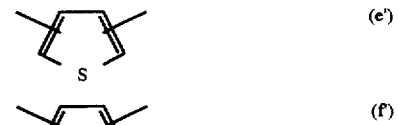

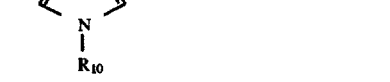

and are useful for the treatment of a wide variety of disease states, whether human or veterinary, for example dermatological, rheumatic, respiratory, cardiovascular, bone and ophthalmological disorders, as well as for the treatment of mammalian skin and hair conditions/disorders.

56 Claims, 3 Drawing Sheets

ADAMANTYL-SUBSTITUTED BIAROMATIC COMPOUNDS AND PHARMACEUTICAL/ COSMETIC COMPOSITIONS COMPRISED THEREOF

CROSS-REFERENCE TO COMPANION APPLICATIONS

Copending applications Ser. No. 08/757,638 filed concurrently herewith, and Ser. No. 08/429,045, filed Apr. 26, 1995 and now U.S. Pat. No. 5,574,036; each is assigned to the assignee hereof.

BACKGROUND OF THE INVENTION

Technical Field of the Invention

The present invention relates to novel adamantyl-substituted biaromatic compounds and to pharmaceutical/ cosmetic compositions comprised thereof; the subject compounds are especially useful in human or veterinary medicine, or, alternatively, in cosmetic compositions.

SUMMARY OF THE INVENTION

The compounds according to the invention display marked activity in the fields of cell differentiation and proliferation and are particularly useful in the topical and systemic treatment of dermatological conditions/afflictions associated with a keratinization disorder, dermatological (or other) conditions/afflictions including an inflammatory and/ or immunoallergic component, and dermal or epidermal proliferations, whether benign or malignant. The subject compounds can, in addition, be used for the treatment of diseases of connective tissue degeneration, to combat aging of the skin, whether photoinduced or chronological, and to treat cicatrization or healing disorders. Moreover, they are also useful for ophthalmological applications, especially for the treatment of corneopathies.

The compounds according to the invention can also be formulated into cosmetic compositions for body and hair care/hygiene.

Briefly, the adamantyl-substituted biaromatic compounds according to this invention have the following structural formula (I):

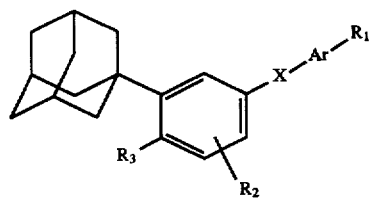

(I)

in which $R_1$ is a —$CH_3$ radical, a —$(CH_2)n$—O—$R_4$ radical, an —O—$(CH_2)m$—$(CO)n$—$R_5$ radical, a —CO—$R_6$ radical, or a —CO—O—$R_7$ radical, wherein the values of m and n and the radicals $R_4$ to $R_7$ are as defined below; $R_2$ is a hydrogen atom, a halogen atom, a linear or branched alkyl radical having from 1 to 20 carbon atoms, an —$OR_4$ radical, or an —O—$CH_2$—O—$CH_2$—$CH_2$—O—$CH_3$ radical; $R_3$ is a —Y—$(CH_2)p$—Y—$(CH_2)q$—$R_8$ radical, a —$(CH_2)p$—Y—$(CH_2)q$—$R_8$ radical, a —Y—$(CH_2)q$—$R_8$ radical, a —CH=CH—$(CH_2)r$—$R_8$ radical, or a —$(CH_2)$q—$R_8$ radical, wherein the values of p, q and r and the radicals Y and $R_8$ are as defined below; X is a bridging radical selected from among those of the following formulae (a)–(k), which may be oriented left-to-right or right-to-left:

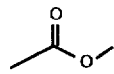 (a)

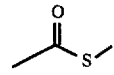 (b)

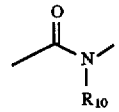 (c)

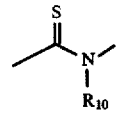 (d)

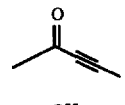 (e)

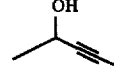 (f)

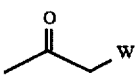 (g)

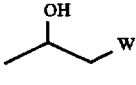 (h)

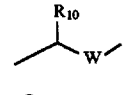 (i)

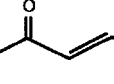 (j)

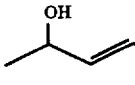 (k)

Ar is a radical selected from among those of the following formulae (a')–(f'):

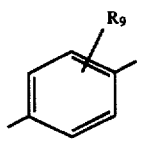 (a')

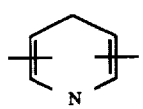 (b')

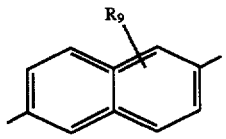 (c')

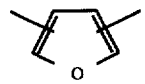 (d')

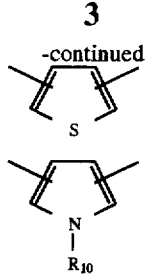

(e')

(f)

m is an integer equal to 1, 2 or 3; n is an integer equal to 0 or 1; p is an integer ranging from 1 to 12, inclusive; q is an integer ranging from 0 to 12, inclusive; r is an integer ranging from 0 to 10, inclusive; t is an integer equal to 0, 1 or 2; Y is an oxygen atom or a radical S(O)t; W is an oxygen atom, a radical S(O)t or a radical N—R$_{10}$; R$_4$ is a hydrogen atom, a lower alkyl radical or a radical —CO—R$_{11}$; R$_5$ is a lower alkyl radical or a heterocycle; R$_6$ is a hydrogen atom, a lower alkyl radical, or a radical:

$$\diagdown_{\underset{R''}{N}}\diagup^{R'}$$

in which R' and R", which may be identical or different, are each a hydrogen atom, a lower alkyl radical, a mono- or polyhydroxyalkyl radical, an optionally substituted aryl radical, or an amino acid or peptide or sugar residue, with the proviso that R' and R" may together form, with the nitrogen atom from which they depend, a nitrogen-containing heterocycle; R$_7$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; R$_8$ is a hydrogen atom, a branched alkyl radical having from 1 to 20 carbon atoms, a C3–C6 cycloaliphatic radical, a monohydroxyalkyl radical or a polyhydroxyalkyl radical, said hydroxyls optionally being protected as methoxy, acetoxy or acetonide groups, an aryl radical, an alkynyl radical, a —CO—R$_6$ radical, a —CO—O—R$_7$ radical, an amino alkyl radical whose amine function is optionally substituted with one or two lower alkyl radicals, or a heterocycle, wherein R$_7$ is as defined above; R$_9$ is a hydrogen or halogen atom, a linear or branched alkyl radical having from 1 to 20 carbon atoms, an —OR$_4$ radical or an —O—CH$_2$—O—CH$_2$—CH$_2$—O—CH$_3$ radical; the radicals R$_{10}$, which may be identical or different, are each a hydrogen atom or a lower alkyl radical; and R$_{11}$ is a lower alkyl radical, with the provisos that (1) when X is a bridging radical of formula (a), (b), (c), (g), (h), (j) or (k), then R$_3$ is other than a radical —Y—(CH$_2$)$_q$—R$_8$, —CH═CH—(CH$_2$),—R$_8$ or —(CH$_2$)$_q$—R$_8$ in which R$_8$ is a hydrogen atom, (2) when X is a bridging radical of formula (a), then R$_3$ is other than the radical —Y—(CH$_2$)$_q$—R$_8$, (3) when X is a bridging radical of formula (b) and R$_3$ is the radical —Y—(CH$_2$)$_q$—R$_8$ in which Y is a sulfur atom, then R$_8$ is other than an aryl radical, and (4) when X is a bridging radical of formula (g), (h), (j) or (k) and R$_3$ is a radical —(CH$_2$)$_q$—R$_8$, then R$_8$ is other than a monohydroxyalkyl or polyhydroxyalkyl radical.

This invention also features the salts of the compounds of formula (I) in the event that R$_1$ or R$_8$ represents a carboxylic acid function and/or when R$_8$ represents an amine function, the chiral (optical) analog and the geometrical isomers thereof. When the compounds according to the invention exist in the form of salts, by addition of an acid, they are pharmaceutically or cosmetically acceptable salts obtained by addition of an inorganic or organic acid thereto, in particular hydrochloric acid, sulfuric acid, acetic acid, citric acid, fumaric acid, hemisuccinic acid, maleic acid and mandelic acid. When the compounds according to the invention are in the form of salts by addition of a base, they are preferably salts of an alkali metal or alkaline earth metal or, alternatively, of zinc or of an organic amine.

Figure 1:
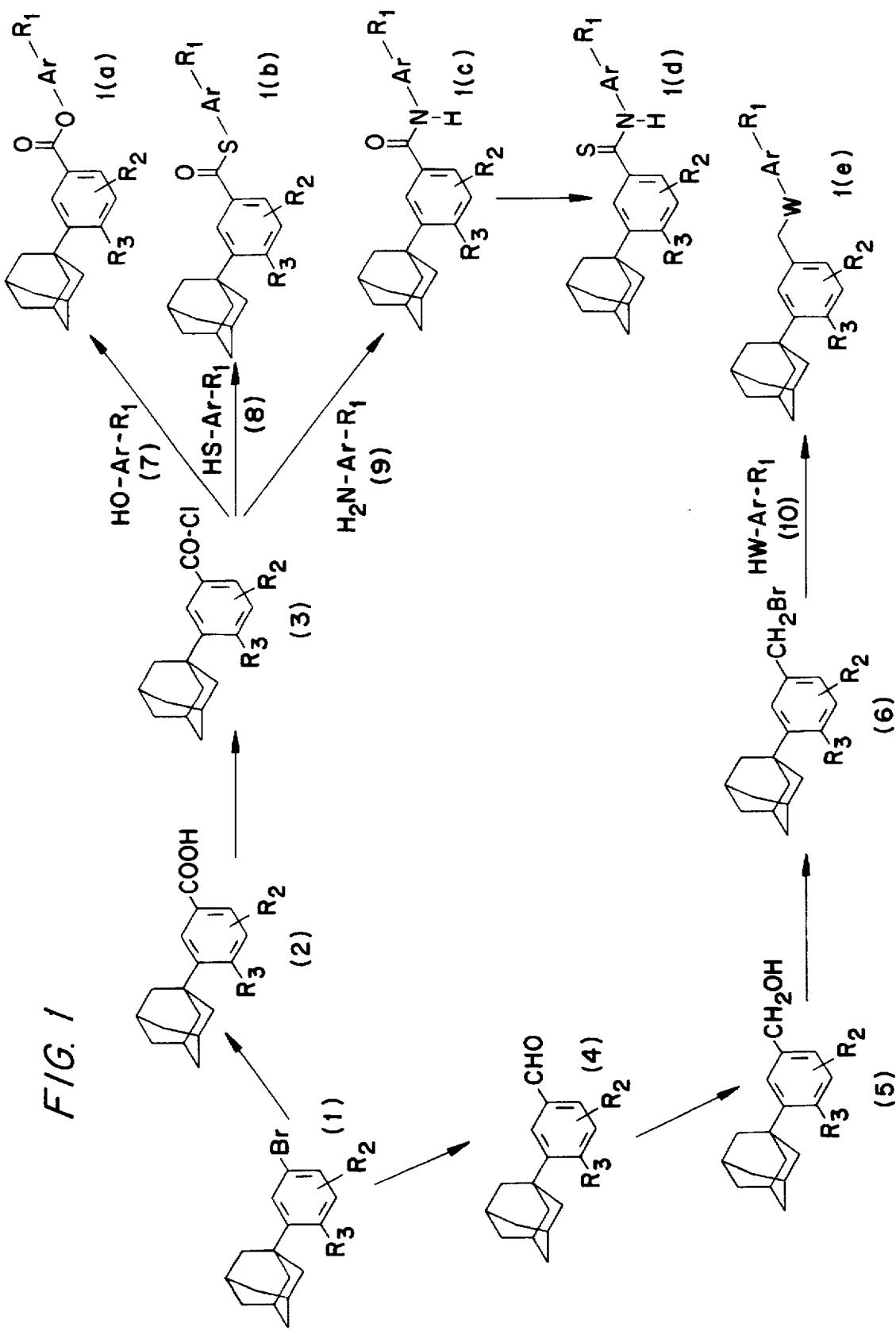
FIGS. 1, 2 and 3 set forth reaction schemes/mechanisms illustrating representative syntheses for the preparation of the adamantyl-substituted biaromatic compounds according to the present invention.

DETAILED DESCRIPTION OF BEST MODE AND SPECIFIC/PREFERRED EMBODIMENTS OF THE INVENTION

More particularly, according to the present invention, by the term "lower alkyl radical" is intended an alkyl radical having from 1 to 12, preferably from 1 to 9, carbon atoms, advantageously the methyl, ethyl, isopropyl, butyl, tert-butyl, hexyl, nonyl and dodecyl radicals.

By the term "linear alkyl radical having from 1 to 20 carbon atoms" is preferably intended the methyl, ethyl, propyl, 2-ethylhexyl, octyl, dodecyl, hexadecyl and octadecyl radicals.

By the term "branched alkyl radical having from 1 to 20 carbon atoms" is preferably intended the 2-methylbutyl, 2-methylpentyl, 1-methylhexyl and 3-methylheptyl radicals.

By "monohydroxyalkyl radical" is intended a radical preferably having 2 or 3 carbon atoms, especially a 2-hydroxyethyl, 2-hydroxypropyl or 3-hydroxypropyl radical.

By "polyhydroxyalkyl radical" is intended a radical preferably having from 3 to 6 carbon atoms and from 2 to 5 hydroxyl groups, such as the 2,3-dihydroxypropyl, 2,3,4-trihydroxybutyl and 2,3,4,5-tetrahydroxypentyl radicals, or the pentaerythritol residue.

By "aryl radical" is preferably intended a phenyl radical optionally substituted by at least one halogen atom, or at least one hydroxyl or nitro functional group.

By "aralkyl radical" is preferably intended the benzyl or phenethyl radical optionally substituted by at least one halogen atom, or at least one hydroxyl or nitro functional group.

By "alkenyl radical" is intended a radical preferably having from 2 to 5 carbon atoms and one or more sites of ethylenic unsaturation, such as, more particularly, the allyl radical.

By the term "sugar residue" is intended a residue derived especially from glucose, from galactose or from mannose, or, alternatively, from glucuronic acid.

By the term "amino acid residue" is especially intended a residue derived from lysine, from glycine or from aspartic acid, and by the term "peptide residue" is more particularly intended a dipeptide or tripeptide residue prepared via the combination of amino acids.

By the term "heterocycle" is preferably intended a piperidino, morpholino, pyrrolidino or piperazino radical, optionally substituted in the 4-position by a C$_1$–C$_6$ alkyl or mono- or polyhydroxyalkyl radical as defined above.

By the term "amino alkyl radical" is preferably intended a radical having from 1 to 6 carbon atoms, in particular the aminomethyl, 3-aminopropyl and 6-aminohexyl radicals.

By "alkynyl radical" is preferably intended a radical having from 2 to 6 carbon atoms, in particular a propargyl radical.

And by "cycloaliphatic radical" is preferably intended a radical having from 3 to 6 carbon atoms, in particular the cyclopropyl and cyclohexyl radicals.

When the radicals $R_2$ and $R_9$ are halogen atoms, they are preferably a fluorine, bromine or chlorine atoms.

Among the compounds of formula (I) according to the present invention, particularly representative are the following:

4-[3-(1-Adamantyl)-4-methoxyphenylthiomethyl]benzoic acid;

4-[3-(1-Adamantyl)-4-methoxyphenylsulfinylmethyl]benzoic acid;

4-[3-(1-Adamantyl)-4-methoxyphenylmethylsulfonyl]benzoic acid;

4-[3-(1-Adamantyl)-4-methoxyphenylmethylsulfinyl]benzoic acid;

4-[3-(1-Adamantyl)-4-methoxyphenylsulfonylmethyl]benzoic acid;

4-[3-(1-Adamantyl)-4-methoxyphenylthiocarboxamido]benzoic acid;

4-[3-(1-Adamantyl)-4-methoxyphenylmethylthio]benzoic acid;

4-[3-(1-Adamantyl)-4-methoxyphenylmethylamino]benzoic acid;

4-[[3-Oxo-3 [3-(1-adamantyl)-4-methoxyphenyl]-1-propynyl]]benzoic acid;

4-[3-(1-Adamantyl)-4-methoxyethoxymethoxybenzamido]benzoic acid;

4-[3-(1-Adamantyl)-4-methoxyethoxymethoxybenzoyloxy]benzoic acid;

(E)-4-[[3-Oxo-3-[3-(1-adamantyl)-4-methoxyethoxymethoxyphenyl]-1-propenyl]]benzoic acid;

4-[[3-Hydroxy-3-[3-(1-adamantyl)-4-methoxyethoxymethoxyphenyl]-1-propynyl]]benzoic acid;

4-[3-(1-Adamantyl)-4-(2,2-dimethyl-1,3-dioxolane-4-methyloxy)phenylcarboxamido]benzoic acid;

4-[3-(1-Adamantyl)-4-(2,3-dihydroxypropyloxy)phenylcarboxamido]benzoic acid;

4-[3-(1-Adamantyl)-4-methoxycarbonylmethyloxyphenylcarboxamido]benzoic acid;

2-[3-(1-Adamantyl)-4-methoxyphenoxymethyl]-4-thiophenecarboxylic acid;

2-[3-(1-Adamantyl)-4-methoxyphenylaminomethyl]-4-thiophenecarboxylic acid;

2-[3-(1-Adamantyl)-4-methoxyphenylthiomethyl]-4-thiophenecarboxylic acid;

4-[3-(1-Adamantyl)-4-(2,2-dimethyl-1,3-dioxolane-4-methyloxy)benzoyloxy]benzoic acid;

4-[3-Hydroxy-3-[5-(1-adamantyl)-2,4-dimethoxyethoxymethoxyphenyl]-1-propynyl]benzoic acid;

4-[3-(1-Adamantyl)-4-methoxyethoxymethoxybenzoylthio]benzoic acid;

N-Methyl-4-[3-(1-adamantyl)-4-methoxyethoxymethoxyphenylcarboxamido]benzoic acid;

4-[3-(1-Adamantyl)-4-methoxyethoxymethoxyphenylthiocarboxamido]benzoic acid;

(E)-4-[[3-Oxo-3-[3-(1-adamantyl)-4-methoxymethoxyphenyl]-1-propenyl]]benzoic acid;

(E)-4-[[3-Oxo-3-[3-(1-adamantyl)-4-hydroxyphenyl]-1-propenyl]]benzoic acid;

(E)-4-[[3-Oxo-3-[3-(1-adamantyl)-4-methoxyphenyl]-1-propenyl]]benzoic acid;

(E)-4-[[3-Oxo-3-[3-(1-adamantyl)-4-(3-hydroxypropyloxy)phenyl]-1-propenyl]]benzoic acid;

4-[3-(1-Adamantyl)-4-methoxyethoxymethoxybenzoyloxy]benzaldehyde;

4-[3-(1-Adamantyl)-4-methoxyethoxymethoxybenzoyloxy]benzenemethanol;

(E)-N-Ethyl-4-[[3-oxo-3-[3-(1-adamantyl)-4-methoxyethoxymethoxyphenyl]-1-propenyl]]benzamide;

(E)-N-(4-Hydroxyphenyl)-4-[[3-oxo-3-[3-(1-adamantyl)-4-methoxyethoxymethoxyphenyl]-1-propenyl]]benzamide;

(E)-4-[[3-Oxo-3-[3-(1-adamantyl)-4-methoxyethoxymethoxyphenyl]-1-propenyl]]phenol.

According to the present invention, the compounds of formula (I) which are the more particularly preferred are those in which at least one, and preferably all, of the following conditions is satisfied:

$R_1$ is the radical —COO—$R_7$ or —CO—$R_6$;

$R_3$ is the radical —Y—$(CH_2)p$—Y—$(CH_2)q$—$R_8$, —$(CH_2)p$—Y—$(CH_2)q$—$R_8$ or —Y—$(CH_2)q$—$R_8$;

X is a bridging radical of formula (a), (e), (f), (j) or (k); and

Ar is a radical of formula (a') or (b').

Figure 2:
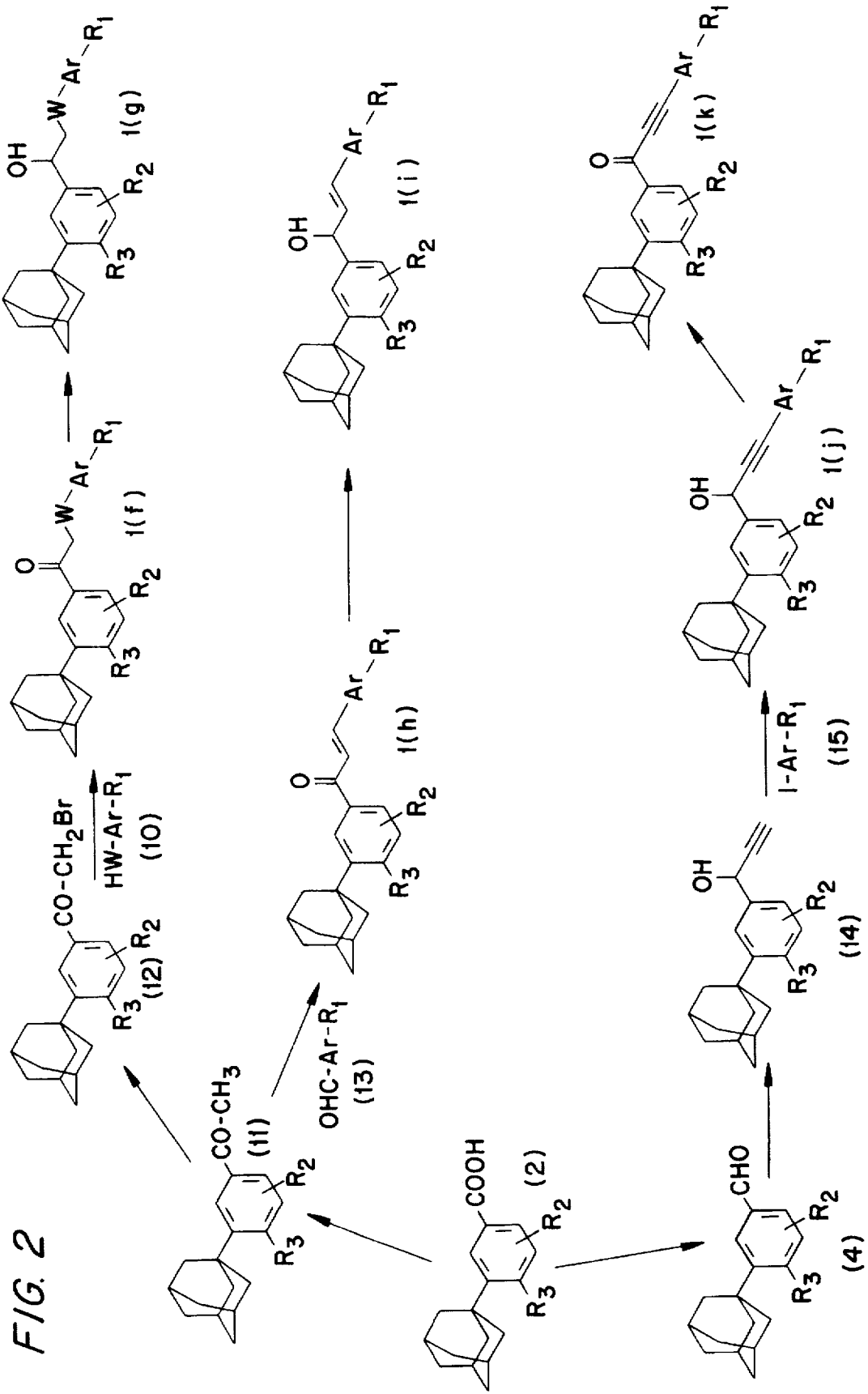
Figure 3:
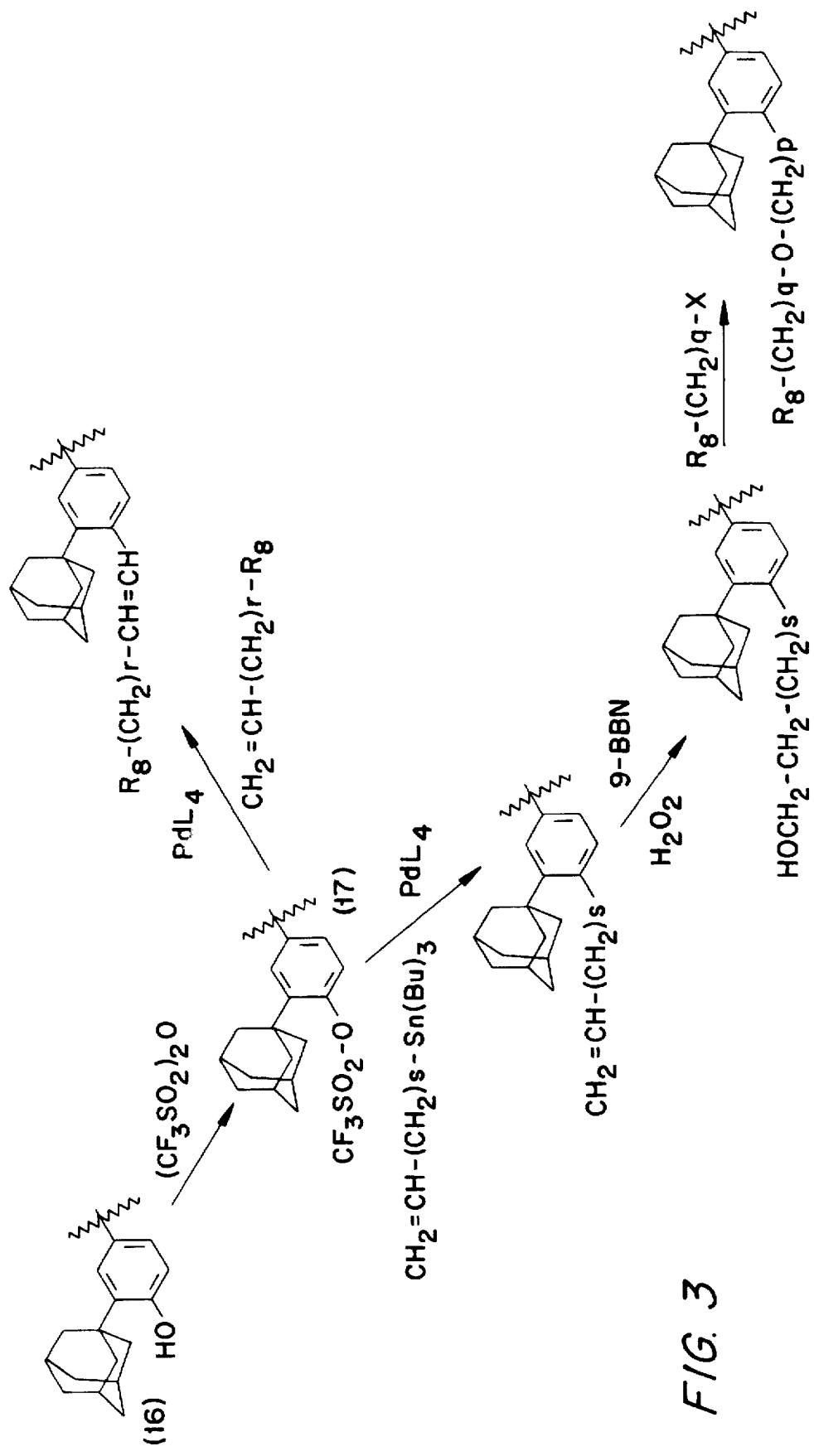

The present invention also features processes for the preparation of the compounds of formula (I), in particular via the reaction schemes illustrated in FIGS. 1, 2 and 3.

Thus, the compounds of formula I(a) can be prepared (FIG. 1) by reacting in anhydrous medium, in an organic solvent, preferably THF, and in the presence of a tertiary amine (for example triethylamine or pyridine), an activated form of a benzoic acid (2), for example an acid chloride (3), with a phenolic compound of formula (7).

The compounds of formula I(b) can be prepared (FIG. 1) by reacting in anhydrous medium, in an organic solvent, preferably THF, and in the presence of a tertiary amine (for example triethylamine or pyridine), an activated form of a benzoic acid (2), for example an acid chloride (3), with a thiophenolic compound of formula (8).

The compounds of formula I(c) can be prepared (FIG. 1) by reacting in anhydrous medium, in an organic solvent, preferably THF, and in the presence of a tertiary amine (for example triethylamine or pyridine), an activated form of an aromatic carboxylic acid (2), for example an acid chloride (3), with an amino compound of formula (9).

The compounds of formula I(d) can be prepared (FIG. 1) from compounds of formula 1(c) via reaction with Lawesson's reagent.

The compounds of formula 1(e) can be prepared (FIG. 1) from benzyl alcohols (5) via conversion of same into bromo derivatives (6) with phosphorus tribromide and then reaction in the presence of potassium carbonate or an alkali metal hydride (sodium hydride), or by phase transfer using, for example, tetrabutylammonium bromide as quaternary salt, with a compound (10) bearing a hydroxyl or thiol or amino functional group.

The compounds of formula I(f) can be prepared (FIG. 2) from acetophenone derivatives (11) via conversion of same into bromo derivative (12) using bromine and then reaction in the presence of potassium carbonate or an alkali metal hydride (sodium hydride), or by phase transfer using, for example, tetrabutylammonium bromide as quaternary salt, with a compound (10) bearing a hydroxyl or thiol or amino functional group.

The compounds of formula I(g) can be prepared from the derivative I(f) by reacting same with sodium borohydride in an alcoholic solvent.

Thus, the compounds of formula I(h) can be prepared (FIG. 2) from acetophenone derivatives (11) by reacting same with aromatic aldehyde derivatives (13) in the presence of sodium methoxide or sodium hydroxide in an alcoholic solvent such as methanol. By reacting these compounds with sodium borohydride in the presence of cerium trichloride, the compounds of formula I(i) are prepared.

And the compounds of formula I(j) can be prepared (FIG. 2) from aromatic aldehyde derivatives (4) by reacting same with lithium trimethylsilylacetylenide and then deprotection or unblocking with tetrabutylammonium fluoride to obtain the α-hydroxyacetylenic derivatives (14). This is followed by coupling with the halo derivatives (15), preferably iodo derivatives, in the presence of a palladium catalyst (for example bis(triphenylphosphine)palladium (II) chloride, in a solvent such as triethylamine. The oxidation of these compounds with either pyridinium dichromate or manganese oxide or the Swern reagent provides the derivatives of formula I(k).

When $R_3$ is a radical —$(CH_2)p$—Y—$(CH_2)q$—$R_8$ or —CH=CH—$(CH_2)$ r—$R_8$, the compounds can be prepared (FIG. 3 in which s is equal to p-2) from phenolic derivatives (16) which are converted into triflate derivatives (17), followed by nucleophilic substitution in the presence of a palladium catalyst, according to the general conditions described in S. Cacchi et al, *Tetrahedron Letters*, 27, 3931–3934 (1986), W. J. Scott et al, *J. Org. Chem.*, 50, 2302–2308 (1985), and J. K. Stille et al, *J. Am. Chem. Soc.*, 109, 5478–5486 (1987).

When $R_1$ is the —COOH radical, the compounds are prepared by protecting $R_1$ with a protecting group of alkyl, allyl, benzyl or tert-butyl type.

Conversion into the free form may be carried out:

(i) in the case of an alkyl protecting group, using sodium hydroxide or lithium hydroxide in an alcoholic solvent such as methanol or in THF;

(ii) in the case of an allylic protecting group, using a catalyst such as certain transition metal complexes in the presence of a secondary amine such as morpholine;

(iii) in the case of a benzylic protecting group, by debenzylation in the presence of hydrogen using a catalyst such as palladium-on-charcoal;

(iv) in the case of a protecting group of tert-butyl type, using trimethylsilyl iodide.

The present invention also features therapeutic/pharmaceutical applications of the compounds of formula (I).

These compounds exhibit activity in the test of differentiation of mouse embryonic teratocarcinoma cells (F9) (*Cancer Research*, 43, p. 5268 (1983)) and/or in the test of inhibition of ornithine decarboxylase after induction with TPA in mice (*Cancer Research*, 38, p. 793–801 (1978)). These tests demonstrate the activities of these compounds in the fields of cell differentiation and proliferation, respectively. In the test of differentiation of the cells (F9), it is possible to evaluate an agonist activity as an antagonist activity towards retinoic acid receptors. An antagonist is inactive when it is alone in this test, but partially or totally inhibits the effect elicited by an agonist retinoid on the morphology and on the secretion of the plasminogen activator. Certain of these compounds therefore also exhibit an activity in a test which entails identifying RAR-antagonist molecules, as described in French patent application No. 95/07302, filed Jun. 19, 1995 and assigned to the assignee hereof. This test comprises the following steps: (i) a sufficient amount of an RAR-agonist molecule is applied topically to an area of the skin of a mammal, (ii) a molecule capable of exhibiting an RAR-antagonist activity is administered systemically or topically to this same mammal or to this same area of the mammal's skin, before, during or after step (i), and (iii) the response by the mammal's skin thus treated is evaluated. Thus, the response to a topical application of an RAR-agonist molecule to the ear of a mammal, which corresponds to an increase in the thickness of this ear, may be inhibited by the systemic or topical administration of an RAR-antagonist molecule.

The compounds according to the invention are particularly well suited in the following fields of therapy:

(1) for treating dermatological conditions/afflictions associated with a keratinization disorder related to differentiation and proliferation, in particular for treating simple acne, comedones, polymorphonuclear leukocytes, rosacea, nodulocystic acne, acne conglobata, senile acne and secondary acnes such as solar, medication-related or occupational acne, (2) for treating other types of keratinization disorders, in particular ichthyosis, ichthyosiform states, Darier's disease, palmoplantar keratoderma, leukoplasias and leukoplasiform states, and cutaneous or mucosal (oral) lichen, (3) for treating other dermatological conditions/afflictions associated with a keratinization disorder manifesting an inflammatory and/or immunoallergic component and, in particular, all forms of psoriasis, whether cutaneous, mucosal or ungual psoriasis, and even psoriatic rheumatism, or alternatively cutaneous atopy, such as eczema or respiratory atopy or, alternatively, gingival hypertrophy; the compounds may also be used in certain inflammatory conditions which do not display any keratinization disorder, (4) for treating all dermal or epidermal proliferations, whether benign or malignant and whether or not of viral origin, such as common warts, flat warts and verruciform epidermodysplasia, and the oral or florid papillomatoses and the proliferations induced by ultraviolet radiation, in particular in the case of basocellular and spinocellular epithelioma, (5) for treating other dermatological disorders such as bullosis and collagen diseases, (6) for treating certain ophthalmological disorders, especially corneopathies, (7) for repairing or combating aging of the skin, whether photoinduced or chronological aging, or for reducing actinic keratoses and pigmentations, or any pathologies associated with chronological or actinic aging, (8) for preventing or curing the stigmata of epidermal and/or dermal atrophy induced by local or systemic corticosteroids, or any other form of cutaneous atrophy, (9) for preventing or treating cicatrization or healing disorders, or for preventing or repairing vibices (stretch marks),

(10) for combating disorders of sebaceous functioning, such as the hyperseborrhoea of acne or simple seborrhoea,

(11) for the treatment or prevention of cancerous or precancerous states,

(12) for the treatment of inflammatory conditions such as arthritis,

(13) for the treatment of any skin or general condition/ affliction of viral origin,

(14) for the prevention or treatment of alopecia,

(15) for the treatment of dermatological or general conditions/afflictions including an immunological component,

(16) for the treatment of conditions/afflictions of the cardiovascular system such as arteriosclerosis.

For the aforesaid therapeutic or pharmaceutical applications, the compounds according to the invention may advantageously be employed in combination with other compounds exhibiting retinoid-type activity, with the D vitamins or derivatives thereof, with corticosteroids, with anti-free-radical agents, with α-hydroxy or α-keto acids or derivatives thereof, or, alternatively, with ion-channel blockers. By the term "D vitamins or derivatives thereof" are intended, for example, derivatives of vitamin $D_2$ or $D_3$ and in particular 1,25-dihydroxyvitamin $D_3$. By the term "anti-free-radical agents" are intended, for example, α-tocopherol, superoxide dismutase, ubiquinol or certain metal-chelating agents. By the term "α-hydroxy or α-keto acids or derivatives thereof" are intended, for example, lactic acid, malic acid, citric acid, glycolic acid, mandelic acid, tartaric acid, glyceric acid or ascorbic acid or the salts, amides or esters thereof. Lastly, by the term "ion-channel blockers" are intended, for example, minoxidil (2,4-diamino-6-piperidinopyrimidine 3-oxide) and derivatives thereof.

The present invention thus also features medicinal compositions containing at least one compound of formula (I), one of the optical or geometrical isomers thereof, or one of the pharmaceutically accepetable salts, or other derivatives thereof.

The pharmaceutical/therapeutic compositions of the present invention, intended especially for the treatment of the aforesaid disease states comprise a pharmaceutically acceptable vehicle, carrier or diluent which is compatible with the mode or regimen of administration selected for the given composition, at least one compound of formula (I), one of the optical or geometrical isomers thereof, or one of the salts, etc., thereof.

The compounds according to the invention may be administered via the systemic, enteral, parenteral, topical or ocular route.

For enteral administration, the medicinal/pharmaceutical compositions may be in the form of tablets, gelatin capsules, dragees, syrups, suspensions, solutions, elixirs, powders, granules, emulsions, microspheres or nanospheres or lipidic or polymeric vesicles which permit a controlled release. For parenteral administration, the compositions may be in the form of solutions or suspensions for infusion or for injection.

The compounds according to the invention are generally administered at a daily dose of approximately 0.01 mg/kg to 100 mg/kg of body weight, and this at the rate or regime of 1 to 3 doses per diem.

For topical administration, the pharmaceutical compositions based on compounds according to the invention are more particularly intended for the treatment of the skin and the mucosae and may then be in the form of pasty ointments, creams, milks, salves, creamy ointments, powders, impregnated pads, solutions, gels, sprays, lotions or suspensions. They may also be in the form of microspheres or nanospheres or lipidic or polymeric vesicles or polymeric patches and hydrogels which permit a controlled release. These topical-route compositions may, moreover, be either in anhydrous form or in an aqueous form, depending on the particular clinical indication.

For ocular administration, they are principally eye drops.

These compositions for topical or ocular application contain at least one compound of formula (I), or one of the optical or geometrical isomers thereof or, alternatively, one of the salts, etc., thereof, at a concentration preferably ranging from 0.001% to 5% by weight relative to the total weight of the composition.

The compounds of formula (I) according to the invention also find application in the cosmetics field, in particular body and hair care/hygiene, and especially for treating skin-types with a tendency towards acne, for promoting the regrowth of the hair, for combating hair loss, for controlling the greasy appearance of the skin or of the hair, for protection against the harmful aspects of the sun or for the treatment of physiologically dry skin-types, and for preventing and/or combating photoinduced or chronological aging.

For cosmetic applications, the compounds according to the invention may, moreover, advantageously be employed in combination with other compounds having retinoid-type activity, with the D vitamins or derivatives thereof, with corticosteroids, with anti-free-radical agents, with α-hydroxy or α-keto acids or derivatives thereof, or, alternatively, with ion-channel blockers, all of these various active agents being as defined above.

The present invention thus also features cosmetic compositions comprising a cosmetically acceptable vehicle suitable for topical application, at least one compound of formula (I), or one of the optical or geometrical isomers thereof, or one of the salts, etc., thereof. Such cosmetic compositions are advantageously in the form of a cream, a milk, a lotion, an ointment, a gel, lipidic or polymeric microspheres or nanospheres or vesicles, a soap or a shampoo.

The concentration of the compound of formula (I) in the cosmetic compositions according to the invention advantageously ranges from 0.001% to 3% by weight relative to the total weight of the composition.

The medicinal and cosmetic compositions according to the invention may additionally contain inert additives and adjuvants, or even pharmacodynamically or cosmetically active additives and adjuvants, or combinations thereof, and especially: wetting agents; depigmenting agents such as hydroquinone, azelaic acid, caffeic acid or kojic acid; emollients; hydrating agents such as glycerol, PEG 400, thiamorpholine and derivatives thereof or alternatively urea; anti-seborrhoeic agents or anti-acne agents such as S-carboxymethylcysteine and S-benzylcysteamine and the salts or derivatives thereof, or benzoyl peroxide; antibiotics such as erythromycin and the esters thereof, neomycin, clindamycin and the esters thereof, and tetracyclines; anti-fungal agents such as ketoconazole or poly-4,5-methylene-3-isothiazolidones; agents promoting the regrowth of the hair, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids and in particular β-carotene; anti-psoriatic agents such as anthraline and derivatives thereof; and, lastly, eicosa-5,8,11,14-tetraynoic acid and eicosa-5,8,11-triynoic acid, and the esters and amides thereof.

The compositions according to the invention may also contain flavor-enhancing agents, preservatives such as parahydroxybenzoic acid esters, stabilizers, moisture regulators, pH regulators, osmotic pressure modifiers, emulsifying agents, UV-A and UV-B screening agents, and antioxidants such as α-tocopherol, butylhydroxyanisole or butylhydroxytoluene.

In order to further illustrate the present invention and the advantages thereof, the following specific examples are given, it being understood that same are intended only as illustrative and in nowise limitative.

EXAMPLE 1

Preparation of 4-[3-(1-adamantyl)-4-methoxyphenylthiomethyl]benzoic acid (a) Preparation of O-3-(1-adamantyl)-4-methoxyphenyl dimethylthiocarbamate 600 mg (20 mmol) of sodium hydride (80% in oil) and 50 ml of DMF were introduced into a round-bottomed flask under a stream of nitrogen. The mixture was cooled to 0° C. and a solution of 5.5 g (20 mmol) of 3-(1-adamantyl)-4-methoxyphenol in 100 ml of DMF was added dropwise, tand he mixture was stirred until the evolution of gas had ceased. A solution of 3.3 g (26 mmol) of dimethylthiocarbamoyl chloride in 50 ml of DMF was then added thereto and the mixture was stirred for eight hours at room temperature. The reaction medium was poured into water and extracted with ethyl acetate. The organic phase was separated out after settling had taken place, washed with water, dried over magnesium sulfate and evaporated. The residue obtained was purified by chromatography on a column of silica, eluted with a mixture of dichloromethane and hexane (70/30). After evaporation of the solvents, 3.1 g (46%) of the expected compound having a melting point of 162°–4° C., were recovered.

(b) Preparation of S-3-(1-adamantyl)-4-methoxyphenyl dimethylthiocarbamate 3 g (8.7 mmol) of the above compound (a) were introduced into a round-bottomed flask under a stream of nitrogen and the mixture was heated at 300° C. for thirty minutes. The reaction medium was extracted with dichloromethane and washed with water. The organic phase was separated out after settling had taken place, dried over magnesium sulfate and evaporated. 2.4 g (80%) of the expected compound, having a melting point of 154°–5° C., were recovered.

(c) Preparation of 3-(1-adamantyl)-4-methoxyphenylthiol 2.3 g (6.6 mmol) of the above compound (b) and 50 ml of methanolic sodium hydroxide solution (2N) were introduced into a round-bottomed flask and the mixture was heated at reflux for three hours. The reaction medium was evaporated and the residue was taken up in water, acidified with concentrated hydrochloric acid and filtered. The residue obtained was purified by chromatography on a column of silica, eluted with a mixture of dichloromethane and hexane (10/90). After evaporation of the solvents, 1.2 g (66%) of the expected thiol derivative, having a melting point of 149°–51° C., was recovered.

(d) Synthesis of 4-[3-(1-adamantyl)-4-methoxyphenylthiomethyl]benzoic acid 1.1 g (36.6 mmol) of sodium hydride (80% in oil) and 50 ml of DMF were introduced into a three-necked flask under a stream of nitrogen. A solution of 4.2 g (15.2 mmol) of 3-(1-adamantyl)-4-methoxyphenylthiol in 20 ml of DMF was added dropwise and the mixture was stirred until the evolution of gas had ceased. A solution of 3.3 g (15.2 mmol) of 4-bromomethylbenzoic acid in 20 ml of DMF was then added and the mixture was stirred at room temperature for eight hours. The reaction medium was poured into water, acidified to pH 1 with hydrochloric acid and extracted with ethyl ether. The organic phase was separated out after settling had taken place, washed with water, dried over magnesium sulfate and evaporated. The residue obtained was purified by chromatography on a column of silica, eluted with a mixture of dichloromethane and ethyl ether (95/5). After evaporation of the solvents, 4.2 g (68%) of the expected compound, having a melting point of 204°–5° C., were recovered.

EXAMPLE 2

Preparation of 4-[3-(1-adamantyl)-4-methoxyohenylsulfinylmethyl]benzoic acid (a) Preparation of methyl 4-[3-(1-adamantyl)-4-methoxyphenylthiomethyl]benzoate 5 g (12.3 mmol) of 4-[3-(1-adamantyl)-4-methoxyphenylthiomethyl]benzoic acid and 50 ml of methanol were introduced into a round-bottomed flask and 330 μl of concentrated sulfuric acid were added. The mixture was heated at reflux for eight hours and the reaction medium was then evaporated to dryness. The residue was taken up in water, neutralized with sodium bicarbonate and extracted with ethyl ether. The organic phase was separated out after settling had taken place, dried over magnesium sulfate and evaporated. The residue obtained was purified by chromatography on a column of silica, eluted with a mixture of dichloromethane and hexane (40/60). After evaporation of the solvents, 4.1 g (79%) of methyl 4-[3-(1-adamantyl)-4-methoxyphenylthiomethyl]benzoate were recovered.

(b) Preparation of methyl 4-[3-(1-adamantyl)-4-methoxyphenylsulfinylmethyl]benzoate 844 mg (2 mmol) of methyl 4-[3-(1-adamantyl)-4-methoxyphenylthiomethyl]benzoate and 20 ml of dichloromethane were introduced into a round-bottomed flask and 386 mg (1.9 mmol) of meta-chloroperbenzoic acid were added. The reaction medium was stirred at room temperature for two hours and was then poured into water and extracted with dichloromethane. The organic phase was separated out after settling had taken place, dried over magnesium sulfate and evaporated. The residue was purified by chromatography on a column of silica, eluted with a mixture of dichloromethane and ethyl ether (90/10). After evaporation of the solvents, 270 mg (30%) of the expected ester, having a melting point of 121°–2° C., were recovered.

(c) Synthesis of 4-[3-(1-adamantyl)-4-methoxyphenylsulfinylmethyl]benzoic acid 1.1 g (2.7 mmol) of the above methyl ester (b), 40 ml of THF and 40 ml of methanolic sodium hydroxide solution (2N) were introduced into a round-bottomed flask and the mixture was stirred at room temperature for eight hours. The reaction medium was evaporated to dryness and the residue was taken up in water, acidified to pH 1 and extracted with ethyl ether. The organic phase was separated out after settling had taken place, dried over magnesium sulfate and evaporated. The residue obtained was triturated from hexane, filtered and dried. 900 mg (78%) of the expected acid, having a melting point of 164°–5° C., were recovered.

EXAMPLE 3

Preparation of 4-[3-(1-adamantyl)-4-methoxyphenylmethylsulfonyl]benzoic acid (a) Preparation of methyl 4-[3-(1-adamantyl)-4-methoxyhenylmethylsulfonyl]benzoate In a manner analogous to that of Example 2(b), 4.22 g (10 mmol) of methyl 4-[3-(1-adamantyl)-4-methoxyphenylmethylthio]benzoate were reacted with 10.35 g (30 mmol) of meta-chloroperbenzoic acid and 1.66 g (37%) of the expected methyl ester, having a melting point of 168°–70° C., was recovered.

(b) Synthesis of 4-[3-(1-adamantyl)-4-methoxyphenylmethylsulfonyl]benzoic acid

In a manner analogous to that of Example 2(c), from 3.98 g (8.7 mmol) of the above methyl ester (a), 3.13 g (81%) of the expected acid, having a melting point of 231°–2° C., were recovered.

EXAMPLE 4

Preparation of 4-[3-(1-adamantyl)-4-methoxyphenylmethylsulfinyl]benzoic acid (a) Preparation of methyl 4-[3-(1-adamantyl)-4-methoxyphenylmethylsulfinyl]benzoate In a manner analogous to that of Example 2(b), 2.96 g (7 mmol) of methyl 4-[3-(1-adamantyl)-4-methoxyphenylmethylthio]benzoate were reacted with 1.42 g (7 mmol) of meta-chloroperbenzoic acid and 2.33 g (76%) of the expected methyl ester, having a melting point of 151°–2° C., were recovered.

(b) Synthesis of 4-[3-(1-adamantyl)-4-methoxyphenylmethylsulfinyl]benzoic acid

In a manner analogous to that of Example 2(c), from 2.7 g (6.2 mmol) of the above methyl ester (a), 2.36 g (90%) of the expected acid, having a melting point of 192°–3° C., were recovered.

EXAMPLE 5

Preparation of 4-[3-(1-adamantyl)-4-methoxyphenylsulfonylmethyl]benzoic acid (a) Preparation of methyl 4-[3-(1-adamantyl)-4-methoxyphenylsulfonylmethyl]benzoate 1.8 g (4.2 mmol) of methyl 4-[3-(1-adamantyl)-4-methoxyphenylthiomethyl]benzoate and 20 ml of dichloromethane were introduced into a round-bottomed flask and 3.4 g (16.9 mmol) of meta-chloroperbenzoic acid were added. The reaction medium was stirred at room temperature for two hours and was then poured into water and extracted with dichloromethane. The organic phase was separated out after settling had taken place, dried over magnesium sulfate and evaporated. The residue was purified by chromatography on a column of silica, eluted with a mixture of dichloromethane and hexane (90/10). After evaporation of the solvents, 1.8 g (93%) of the expected ester, having a melting point of 166°–8° C., was recovered.

(b) Synthesis of 4-[3-(1-adamantyl)-4-methoxyphenylsulfonylmethyl]benzoic acid

In a manner analogous to that of Example 2(a), from 2.1 g (4 mmol) of the above methyl ester (a), 1.3 g (68%) of the expected acid, having a melting point of 238°–9° C., was recovered.

EXAMPLE 6

Preparation of 4-[3-(1-adamantyl)-4-methoxyphenylthiocarboxamido]benzoic acid (a) Preparation of methyl 4-[3-(1-adamantyl)-4-methoxyphenylthiocarboxamido]benzoate 6.7 g (18.6 mmol) of methyl 4-[3-(1-adamantyl)-4-methoxyphenylcarboxamido]benzoate and 60 ml of toluene were introduced into a round-bottomed flask and 4.1 g (9.9 mmol) of Lawesson's reagent were added. The reaction medium was heated at reflux for three hours and was then evaporated to dryness. The residue obtained was taken up in water and dichloromethane. The organic phase was separated out after settling had taken place, dried over magnesium sulfate and evaporated. The residue obtained was purified by chromatography on a column of silica, eluted with dichloromethane. After evaporation of the solvents, 6 g (83%) of the expected ester, having a melting point of 198°–200° C., were recovered.

(b) Synthesis of 4-[3-(1-adamantyl)-4-methoxyphenylthiocarboxamido]benzoic acid

In a manner analogous to that of Example 2(a), from 6 g (14.3 mmol) of the above methyl ester (a), 5.6 g (92%) of the expected acid, having a melting point of 255°–6° C., were recovered.

EXAMPLE 7

Preparation of 4-[3-(1-adamantyl)-4-methoxyphenylmethylthio]benzoic acid (a) Preparation of 3-(1-adamantyl)-4-methoxybenzenemethanol 8 g (0.2 mol) of lithium aluminum hydride and 50 ml of anhydrous THF were introduced into a three-necked flask under a stream of nitrogen. A solution of 28.6 g (0.1 mol) of 3-(1-adamantyl)-4-methoxybenzoic acid in 260 ml of anhydrous THF was added dropwise and the mixture was heated at reflux for 16 hours. The reaction medium was cooled and hydrolyzed with 14.4 ml of sodium potassium tartrate solution. The salt was filtered off. The filtrate was evaporated and the solid obtained was triturated from hexane, filtered off and dried. 26.2 g (96%) of the expected benzyl alcohol, having a melting point of 134°–5° C., were recovered.

(b) Preparation of 3-(1-adamantyl)-4-methoxybenzyl bromide 2.72 g (10 mmol) of the above benzyl alcohol (a), 30 ml of toluene and 800 µl (10 mmol) of pyridine were introduced into a three-necked flask. A solution of 940 µl (10 mmol) of phosphorus tribromide in 9 ml of toluene was added dropwise, at 0° C., and the mixture was stirred at room temperature for 4 hours. The reaction medium was evaporated to dryness and the residue was taken up in water and ethyl ether. The organic phase was separated out after settling had taken place, dried over magnesium sulfate and evaporated. The residue obtained was triturated from hexane, filtered and dried. 2.35 g (70%) of the expected benzyl bromide, having a melting point of 95°–9° C., were recovered.

(c) Preparation of methyl 4-[3-(1-adamantyl)-4-methoxyphenylmethylthio]benzoate 1.44 g (48 mmol) of sodium hydride (80% in oil) and 25 ml of DMF were introduced into a three-necked flask under a stream of nitrogen. A solution of 6.73 g (40 mmol) of methyl 4-mercaptobenzoate in 60 ml of DMF was added dropwise and the mixture was stirred until the evolution of gas had ceased. A solution of 16.1 g (48 mmol) of 3-(1-adamantyl)-4-methoxybenzyl bromide in 90 ml of DMF was then added and the mixture was stirred at room temperature for eight hours. The reaction medium was poured into water, acidified to pH 1 with hydrochloric acid and extracted with ethyl ether. The organic phase was separated out after settling had taken place, washed with water, dried over magnesium sulfate and evaporated. The residue obtained was purified by chromatography on a column of silica eluted with a mixture of dichloromethane and hexane (40/60). After evaporation of the solvents, 16.75 g (99%) of the expected methyl ester, having a melting point of 143°–5° C., were recovered.

(d) Synthesis of 4-[3-(1-adamantyl)-4-methoxyphenylmethylthio]benzoic acid

In a manner analogous to that of Example 2(a), from 4.22 g (10 mmol) of the above methyl ester (c), 3.15 g (77%) of the expected acid, having a melting point of 225°–7° C., were recovered.

EXAMPLE 8

Preparation of 4-[3-(1-adamantyl)-4-methoxyphenylmethylamino]benzoic acid (a) Preparation of benzyl N-tert-butyloxycarbonyl-3-(1-adamantyl)-4-methoxyophenylmethylamino]benzoate In a manner analogous to that of Example 7(c), 10.6 g (34.6 mmol) of 3-(1-adamantyl)-4-methoxybenzyl bromide were reacted with 8.6 g (26.3 mmol) of benzyl 4-tert-butyloxycarboxamidobenzoate, and 14 g (91%) of the expected benzyl ester were recovered in the form of a yellow oil.

(b) Preparation of benzyl 3-(1-adamantyl)-4-methoxyphenylmethylamino]benzoate 13.96 g (24 mmol) of the above benzyl ester (a) and 100 ml of carbon tetrachloride were introduced into a three-necked flask under a stream of nitrogen. 5 ml (48 mmol) of trimethylsilyl iodide were added dropwise and the mixture was stirred at room temperature for 12 hours. The reaction medium was poured into water and extracted with ethyl ether. The organic phase was separated out after settling had taken place, dried over magnesium sulfate and evaporated. The residue obtained was purified by chromatography on a column of silica, eluted with a mixture of dichloromethane and hexane (55/45). After evaporation of the solvents, 6.64 g (57%) of the expected benzyl ester were recovered.

(c) Synthesis of 4-[3-(1-adamantyl)-4-methoxyphenylmethylamino]benzoic acid

In a manner analogous to that of Example 2(a), from 1.44 g (3 mmol) of the above benzyl ester, 877 mg (75%) of the expected acid, having a melting point of 259°–60° C., were recovered.

EXAMPLE 9

Preparation of 4-[[3-oxo-3-[3-(1-adamantyl)-4-methoxyphenyl]-1-propynyl]]benzoic acid (a) Preparation of methyl 4-trimethylsilylethynylbenzoate 21.5 g (0.1 mol) of methyl 4-bromobenzoate, 300 ml of triethylamine and a mixture of 200 mg of palladium acetate and 400 mg of triphenylphosphine were introduced into a three-necked flask under a stream of nitrogen. 20 g (0.204 mmol) of trimethylsilylacetylene were then added and the mixture was heated gradually to 90° C. over 1 hour and maintained at this temperature for 5 hours. The reaction medium was cooled, the salt was filtered off and the filtrate was evaporated. The residue was taken up in 200 ml of hydrochloric acid (5%) and 400 ml of ethyl ether. The ether phase was separated out after settling had taken place, washed with water, dried over magnesium sulfate and evaporated. The residue obtained was purified by chromatography on a column of silica, eluted with dichloromethane. After evaporation of the solvents, 23 g (100%) of the compound were recovered in the form of a colorless oil.

(b) Preparation of methyl 4-[[3-oxo-3-[3-(1-adamantyl)-4-methoxyphenyl]-1-propynYl]]benzoate 3 g (10 mmol) of 3-(1-adamantyl)-4-methoxybenzoyl chloride, 2.3 g (10 mmol) of the above compound (a) and 100 ml of dichloromethane were introduced into a round-bottomed flask. 4.7 g (35 mmol) of AlCl$_3$ were added portionwise, at 0° C., and the mixture was stirred at room temperature for 8 hours. The reaction medium was poured into ice and extracted with dichloromethane. The organic phase was separated out after settling had taken place, dried over magnesium sulfate and evaporated. The residue obtained was purified by chromatography on a column of silica, eluted with a mixture of dichloromethane and hexane (80/20). 970 mg (23%) of the expected compound, having a melting point of 156°–8° C., were recovered.

(c) Synthesis of 4-[[3-oxo-3-[3-(1-adamantyl)-4-methoxyphenyl]-1-propynyl]]benzoic acid 962 mg (2.2 mmol) of the above methyl ester (b) and 10 ml of THF were introduced into a round-bottomed flask and 283 mg (6.7 mmol) of lithium hydroxide were added. The reaction medium was heated at reflux for 5 hours and was then poured into water and acidified to pH 1 with concentrated hydrochloric acid. The organic phase was separated out after settling had taken place, dried over magnesium sulfate and evaporated. The solid obtained was triturated from hexane, filtered off and dried. 600 mg (85%) of the expected acid, having a melting point of 232°–4° C., were recovered.

EXAMPLE 10

Preparation of 4-[3-(1-adamantyl)-4-methoxyethoxymethoxybenzamido]benzoic acid (a) Preparation of 3-(1-adamantyl)-1-bromo-4-methoxyethoxymethoxybenzene 3.8 g (0.13 mol) of sodium hydride (80% in oil) and 50 ml of DMF were introduced into a three-necked flask under a stream of nitrogen and a solution of 40 g (0.13 mol) of 2-(1-adamantyl)-4-bromophenol in 100 ml of DMF was added dropwise. The mixture was stirred until the evolution of gas had ceased. A solution of 18 ml (0.15 mol) of 2-methoxyethoxymethyl chloride in 20 ml of DMF was then added dropwise and the mixture was stirred for four hours at room temperature. The reaction medium was poured into water and extracted with ethyl ether. The organic phase was separated out after settling had taken place, washed with water, dried over magnesium sulfate and evaporated. The residue was purified by chromatography on a column of silica, eluted with a mixture of dichloromethane and hexane (50/50). After evaporation of the solvents, 40.1 g (78%) of the expected compound, having a melting point of 69°–70° C., were recovered.

(b) Preparation of 3-(1-adamantyl)-4-methoxyethoxymethoxybenzoic acid

The above compound (a) (28.5 g, 72 mmol) was dissolved in 200 ml of THF. The solution obtained was added dropwise to magnesium (2.4 g, 100 mmol) and a crystal of iodine. After introduction, the mixture was heated at reflux for two hours, cooled to –78° C. and a stream of CO$_2$ was passed therethrough for one hour. The reaction medium was permitted to warm to room temperature and was then poured into saturated aqueous ammonium chloride solution and extracted with ethyl ether. The organic phase was separated out after settling had taken place, dried over magnesium sulfate and evaporated. The residue obtained was triturated from hexane, filtered and dried. 15.5 g (60%) of the expected acid, having a melting point of 115°–6° C., were recovered.

(c) Preparation of 3-(1-adamantyl)-4-methoxyethoxymethoxybenzoyl chloride

A solution of 3 g (8.3 mmol) of 3-(1-adamantyl)-4-methoxyethoxymethoxybenzoic acid in 50 ml of anhydrous dichloromethane was introduced into a round-bottomed flask. 1.7 ml (8.3 mmol) of dicyclohexylamine was added and the mixture was stirred for one hour. 600 µl (8.3 mmol) of thionyl chloride were then added and the mixture was stirred for one hour. It was evaporated to dryness, the residue was taken up in anhydrous ethyl ether, the dicyclohexylamine salt was filtered off and the filtrate was evaporated. 3.3 g (100%) of the crude acid chloride, which was used without further purification for the remainder of the synthesis, were recovered.

(d) Preparation of allyl 4-[3-(1-adamantyl)-4-methoxyethoxymethoxybenzamido]benzoate 700 mg (3.95 mmol) of allyl 4-aminobenzoate, 1 ml (4.3 mmol) of triethylamine and 50 ml of THF were introduced into a round-bottomed flask. A solution of 1.5 g (3.96 mmol) of 3-(1-adamantyl)-4-methoxyethoxymethoxybenzoyl chloride was added dropwise and the mixture was stirred at room temperature for 4 hours. The reaction medium was poured into water and extracted with ethyl ether. The organic phase was separated out after settling had taken place, dried over magnesium sulfate and evaporated. The residue obtained was purified by chromatography on a column of silica, eluted with dichloromethane. 1.7 g (83%) of the expected allylic ester was recovered in the form of an oil.

(e) Synthesis of 4-[3-(1-adamantyl)-4-methoxyethoxnmethoxybenzamido]benzoic acid 1.7 g (3.2 mmol) of the above allylic ester, 50 ml of THF and 200 mg of tetrakis(triphenylphosphine)Pd(0) were introduced into a three-necked flask under a stream of nitrogen. A solution of sodium diethyl malonate, prepared from 105 mg (3.5 mmol) of sodium hydride (80% in oil) and 500 µl (3.2 mmol) of diethyl malonate, was added dropwise and the mixture was stirred at room temperature for 2 hours. The reaction medium was evaporated to dryness and the residue was taken up in water, acidified to pH 4 and extracted with ethyl ether. The organic phase was separated out after settling had taken place, dried over magnesium sulfate and evaporated. The residue obtained was purified by chromatography on a column of silica, eluted with ethyl ether. 1.1 g (70%) of the expected acid, having a melting point of 150°–2° C., was recovered.

EXAMPLE 11

Preparation of 4-[3-(1-adamantyl)-4-methoxyethoxymethoxybenzoyloxy]benzoic acid (a) Preparation of allyl 4-[3-(1-adamantyl)-4-methoxyethoxymethoxybenzoyloxy]benzoate:

In a manner analogous to that of Example 10(d), 1.5 g (3.9 mmol) of 3-(1-adamantyl)-4-methoxyethoxymethoxybenzoyl chloride was reacted with 705 mg (3.9 mmol) of allyl 4-hydroxybenzoate, and 1.45 g (70%) of the expected allylic ester was recovered in the form of a yellow oil.

(b) Synthesis of 4-[3-(1-adamantyl)-4-methoxyethoxymethoxybenzoyloxy]benzoic acid In a manner analogous to that of Example 10(e), from 1.45 g (2.8 mmol) of the above allylic ester (a), 870 mg (65%) of the expected acid, having a melting point of 211°–3° C., were recovered.

EXAMPLE 12

Preparation of (E)-4-[[3-oxo-3-[3-(1-adamantyl)-4-methoxyethoxymethoxyphenyl]-1-propenyl]]benzoic acid (a) Preparation of 3-(1-adamantyl)-4-methoxyethoxymethoxyacetophenone:

15.5 g (43 mmol) of 3-(1-adamantyl)-4-methoxyethoxymethoxybenzoic acid and 300 ml of anhydrous ethyl ether were introduced into a three-necked flask under a stream of nitrogen. 80 ml (0.13 mol) of methyllithium (1.6M in ether) were added dropwise, at –20° C., and the mixture was then stirred for three hours at room temperature. The reaction medium was poured into saturated aqueous ammonium chloride solution and the organic phase was separated out after settling had taken place, dried over magnesium sulfate and evaporated. 15.4 g (100%) of the expected acetophenone were recovered in the form of a pale yellow oil.

(b) Preparation of methyl (E)-4-[[3-oxo-3-[3-(1-adamantyl)-4-methoxyethoxymethoxypnhenyl]-1-propenyl]]benzoate 1.8 g (5 mmol) of 3-(1-adamantyl)-4-methoxyethoxymethoxyacetophenone, 820 mg (5 mmol) of methyl 4-formylbenzoate and 20 ml of methanol were introduced into a round-bottomed flask. 10 mg of 18-crown-6 and 200 mg of sodium hydroxide pellets were added and the mixture was stirred at room temperature for 4 hours. It was evaporated to dryness and the residue obtained was purified by chromatography on a column of silica, eluted with dichloromethane. 1.4 g (55%) of the expected methyl ester was recovered.

(c) Synthesis of (E)-4-[[3-oxo-3-[3-(1-adamantyl)-4-methoxyethoxymethoxyphenyl]-1-propenyl]]benzoic acid In a manner analogous to that of Example 2(a), from 700 mg (1.4 mmol) of methyl (E)-4-[[3-oxo-3-[3-(1-adamantyl)-4-methoxyethoxymethoxyphenyl]-1-propenyl]]benzoate, 590 mg (87%) of the expected acid, having a melting point of 154°–6° C., were recovered.

EXAMPLE 13

Preparation of 4-[[3-hydroxy-3-[3-(1-adamantyl)-4-methoxyethoxymethoxyphenyl]-1-propynyl]]benzoic acid (a) Preparation of 3-(1-adamantyl)-4-methoxyethoxymethoxyphenylcarboxaldehyde 34 g (89 mmol) of 3-(1-adamantyl)-1-bromo-4-methoxyethoxymethoxybenzene and 250 ml of THF were introduced into a three-necked flask under a stream of nitrogen. 43 ml (106 mmol) of n-butyllithium solution (2.5M in hexane) were added dropwise, at –78° C., and the mixture was stirred for 30 min. 8.3 ml (106 mmol) of DMF were then added dropwise and the mixture was permitted to warm to room temperature. The reaction medium was poured into aqueous ammonium chloride solution and extracted with ethyl ether. The organic phase was separated out after settling had taken place, dried over magnesium sulfate and evaporated. The residue obtained was purified by chromatography on a column of silica, eluted with dichloromethane. After evaporation of the solvents, 17.6 g (58%) of the expected aldehyde, having a melting point of 63°–4° C., were recovered.

(b) Preparation of a-trimethylsilylethynyl-3-(1-adamantyl)-4-methoxyethoxymethoxyphenyl methanol 1.7 ml (11.9 mmol) of trimethylsilylacetylene and 25 ml of THF were introduced into a three-necked flask. A solution of 5 ml (11.9 mmol) of n-butyllithium (2.5M in hexane) was added dropwise, at –78° C. and under a stream of nitrogen, and the mixture was permitted to warm to room temperature. This solution was introduced dropwise into a solution of 3.7 g (10.7 mmol) of 3-(1-adamantyl)-4-methoxyethoxymethoxyphenylcarboxaldehyde in 50 ml of THF, at –78° C. The reaction medium was permitted to warm to room temperature, poured into aqueous ammonium chloride solution and extracted with ethyl ether. The organic phase was separated out after settling had taken place, dried over magnesium sulfate and evaporated. 4.7 g (97%) of the expected alcohol were recovered in the form of a yellow oil.

(c) Preparation of a-ethynyl-3-(1-adamantyl)-4-methoxyethoxymethoxyphenylmethanol 4.7 g (10.5 mmol) of a-trimethylsilylethynyl-3-(1-adamantyl)-4-methoxyethoxymethoxyphenylmethanol and 50 ml of THF were introduced into a round-bottomed flask and 11.4 ml (12.6 mmol) of tetrabutylammonium fluoride solution (1.1M in THF) was added dropwise. The reaction medium was stirred at room temperature for one hour and was then poured into water and extracted with ethyl ether. The organic phase was separated out after settling had taken place, dried over magnesium sulfate and evaporated. The residue obtained was purified by chromatography on a column of silica, eluted with a mixture of ethyl acetate and heptane (30/70). After evaporation of the solvents, 2.5 g (64%) of a-ethynyl-3-(1-adamantyl)-4-methoxyethoxymethoxyphenyl-methanol were recovered.

(d) Preparation of methyl 4-[[3-hydroxy-3-[3-(1-adamantyl)-4-methoxyethoxymethoxyphenyl]-1-propynyl]]benzoate 2.5 g (6.7 mmol) of a-ethynyl-3-(1-adamantyl)-4-methoxyethoxymethoxyphenylmethanol, 1.2 g (6.7 mmol) of methyl 4-iodobenzoate and 50 ml of triethylamine were introduced into a three-necked flask. The reaction medium was degassed with nitrogen for 30 min, then 380 mg (0.5 mmol) of bis(triphenylphosphine)palladium (II) chloride and 190 mg (0.8 mmol) of copper iodide were successively added. The reaction medium was stirred at room temperature for four hours and was then evaporated to dryness and the residue obtained was taken up in water and ethyl ether. The organic phase was separated out after settling had taken place, dried over magnesium sulfate and evaporated. The residue obtained was purified by chromatography on a column of silica, eluted with a mixture of ethyl acetate and heptane (20/80). 2.7 g (79%) of methyl 4-[[3-hydroxy-3-[3-(1-adamantyl)-4-methoxyethoxymethoxyphenyl]-1-propynyl]]benzoate, having a melting point of 95°–6° C., were recovered.

(e) Synthesis of 4-[[3-Hydroxy-3-[3-(1-adamantyl)-4-methoxyethoxymethoxyphenyl]-1-propynyl]]benzoic acid In a manner analogous to that of Example 9(c), from 2.66 g (5.3 mmol) of the above methyl ester (d), 1.52 g (88%) of the expected acid, having a melting point of 148°–9° C., was recovered.

EXAMPLE 14

Preparation of 4-[3-(1-adamantyl)-4-(2,2-dimethyl-1,3-dioxolane-4-methyloxy)phenylcarboxamido]benzoic acid (a) Preparation of methyl 3-(1-adamantyl)-4-(2,2-dimethyl-1,3-dioxolane-4-methyloxy)benzoate To a solution of 10 g (0.0349 mol) of methyl 3-(1-adamantyl)-4-hydroxybenzoate in 100 ml of DMF containing 5.31 g (0.0384 mol) of potassium carbonate was added dropwise a solution of 12 g (0.0419 mol) of 3-tosyloxy-1, 2-propanediolacetonide. The reaction medium was heated at 100° C. for twelve hours and then poured into icewater and extracted with ethyl ether. The organic phase was separated out after settling had taken place, dried over sodium sulfate and evaporated. The residue was purified by chromatography on a column of silica, eluted with a mixture of hexane and ethyl acetate (80/20). After evaporation of the solvents, 8.8 g (63%) of the expected compound, having a melting point of 158°–9° C., were recovered.

(b) Preparation of 3-(1-adamantyl)-4-(2,2-dimethyl-1,3-dioxolane-4-methyloxy)benzoic acid 8.8 g (0.022 mol) of the above methyl ester (a) and 200 ml of methanolic sodium hydroxide solution (2N) were introduced into a round-bottomed flask. The mixture was heated at reflux for three hours and was evaporated to dryness. The residue was taken up in an ethyl ether/water mixture and acidified to pH 3. The organic phase was separated out after settling had taken place, dried over magnesium sulfate and evaporated. The solid obtained was triturated from hexane, filtered off and dried. 8.3 g (98%) of the expected acid, having a melting point of 224°–5° C., were recovered.

(c) Preparation of 3-(1-adamantyl)-4-(2,2-dimethyl-1,3-dioxolane-4-methyloxy)benzoyl chloride 8.3 g (0.0215 mol) of 3-(1-adamantyl)-4-(2,2-dimethyl-1,3-dioxolane-4-methyloxy)benzoic acid, 80 ml of dichloromethane and 4.3 ml (0.0216 mol) of dicyclohexylamine were introduced into a round-bottomed flask. The mixture was stirred for one hour at room temperature and 1.7 ml (0.0236 mol) of thionyl chloride are then introduced. The mixture was stirred for four hours and was evaporated to dryness. The residue was taken up in ethyl ether, the dicyclohexylamine salt was filtered off, the filtrate was evaporated and 8.5 g (100%) of acid chloride, which was used without further purification in the remainder of the synthesis, were recovered.

(d) Preparation of methyl 4-[3-(1-adamantyl)-4-(2,2-dimethyl-1,3-dioxolane-4-methyloxy)phenylcarboxamido]benzoate 1.62 g (10.7 mmol) of methyl 4-aminobenzoate, 30 ml of THF and 1.65 ml (11.8 mmol) of triethylamine were introduced into a round-bottomed flask. A solution of 4.3 g (10.7 mmol) of 3-(1-adamantyl)-4-(2,2-dimethyl-1,3-dioxolane-4-methyloxy)benzoyl chloride in 30 ml of THF was added dropwise and the mixture was stirred at room temperature for sixteen hours. The reaction medium was poured into water and extracted with ethyl ether. Thehe organic phase was separated out after settling had taken place, dried over magnesium sulfate and evaporated. The residue obtained was purified by chromatography on a column of silica, eluted with a mixture of dichloromethane and ethyl ether (98/2). 3.1 g (56%) of the expected methyl ester, having a melting point of 174°–5° C., were recovered.

(e) Synthesis of 4-[3-(1-adamantyl)-4-(2,2-dimethyl-1,3-dioxolane-4-methyloxy)-phenylcarboxamido]benzoic acid In a manner analogous to that of Example 14(b), from 1 g (1.92 mmol) of the above methyl ester, 900 mg (93%) of 4-[3-(1-adamantyl)-4-(2,2-dimethyl-1,3-dioxolane-4-methyloxy)phenylcarboxamido]benzoic acid, having a melting point of 245°–6° C., were recovered.

EXAMPLE 15

Preparation of 4-[3-(1-adamantyl)-4-(2,3-dihydroxypropyloxy)phenylcarboxamido]benzoic acid (a) Preparation of methyl 4-[3-(1-adamantyl)-4-(2,3-dihydroxypropyloxy)phenylcarboxamido]benzoate 1.96 g (3.78 mmol) of methyl 4-[3-(1-adamantyl)-4-(2,2-dimethyl-1,3-dioxolane-4-methyloxy)phenylcarboxamido]benzoate, 70 ml of dichloromethane and 8 ml of THF were introduced into a round-bottomed flask and 7.24 g (38 mmol) of para-toluenesulfonic acid were added. The reaction medium was stirred at room temperature for four hours and was then poured into water and extracted with ethyl ether. The organic phase was separated out after settling had taken place, dried over magnesium sulfate and evaporated. The residue obtained was purified by chromatography on a column of silica, eluted with a mixture of ethyl acetate and dichloromethane (90/10). 1.46 g (81%) of the expected compound, having a melting point of 111°–2° C., was recovered.

(b) Synthesis of 4-[3-(1-adamantyl)-4-(2,3-dihydroxypropyloxy)phenylcarboxamido]benzoic acid In a manner analogous to that of Example 14(b), from 1.42 g (2.96 mmol) of the above methyl ester (a), 650 mg (47%) of 4-[3-(1-adamantyl)-4-(2,3-dihydroxypropyloxy) phenylcarboxamido]benzoic acid, having a melting point of 236°–7° C., were recovered.

EXAMPLE 16

Preparation of 4-[3-(1-adamantyl)-4-methoxycarbonylmethyloxyphenylcarboxamido]benzoic acid (a) Preparation of benzyl 3-(1-adamantyl)-4-methoxycarbonylmethyloxybenzoate 2.1 g (5.79 mmol) of benzyl 3-(1-adamantyl)-4-hydroxybenzoate and 20 ml of DMF were introduced into a three-necked flask and 191 mg (6.34 mmol) of sodium hydride (80% in oil) were added portionwise. The mixture was stirred until the evolution of gas had ceased, then 565 µl (5.79 mmol) of methyl bromoacetate were added and the mixture was stirred at room temperature for twelve hours. The reaction medium was poured into water and extracted with ethyl ether. The organic phase was separated out after settling had taken place, dried over magnesium sulfate and evaporated. The solid was triturated from hexane, filtered off and dried. 2.36 g (94%) of the expected compound, having a melting point of 134°–5° C., were recovered.

(b) Preparation of 3-(1-adamantyl)-4-methoxycarbonylmethyloxybenzoic acid 2.34 g (5.38 mmol) of benzyl 3-(1-adamantyl)-4-methoxycarbonylmethyloxybenzoate, 40 ml of dioxane, 500 µl of acetic acid and 234 mg of palladium (10%) were introduced into a reactor. The mixture was hydrogenated at 40° C. and at a pressure of 7 bar for three hours. The catalyst was filtered off and the mixture was evaporated to dryness. The solid obtained was triturated from hexane, filtered off and dried. 1.74 g (94%) of the expected acid, having a melting point of 230°–1° C., was recovered.

(c) Preparation of 3-(1-adamantyl)-4-methoxycarbonylmethyloxybenzoyl chloride 1.78 g (5 mmol) of 3-(1-adamantyl)-4-methoxycarbonylmethyloxybenzoic acid and 15 ml of thionyl chloride were introduced into a round-bottomed flask and the mixture was heated at reflux for one hour. It was evaporated to dryness and the crude acid chloride, which was used without further purification in the remainder of the synthesis, was recovered.

(d) Preparation of benzyl 4-[3-(1-adamantyl)-4-methoxycarbonylmethyloxyphenyl-carboxamido]benzoate In a manner analogous to that of Example 14(d), 1.13 g (5 mmol) of benzyl 4-aminobenzoate was reacted with 1.8 g (5 mmol) of 3-(1-adamantyl)-4-methoxycarbonylmethyloxybenzoyl chloride and 1.7 g (61%) of the expected benzyl ester, having a melting point of 95°–6° C., was recovered.

(e) Synthesis of 4-[3-(1-adamantyl)-4-methoxycarbonylmethyloxyphenylcarboxamido]benzoic acid In a manner analogous to that of Example 16(b), from 1.69 g (3 mmol) of benzyl 4-[3-(1-adamantyl)-4-methoxycarbonylmethyloxyphenylcarbox-amido]benzoate, 1.13 g (80%) of the expected acid, having a melting point of 291°–2° C., was recovered.

EXAMPLE 17

Preparation of 2-[3-(1-adamantyl)-4-methoxyphenoxymethyl]-4-thiophenecarboxylic acid (a) Preparation of methyl 2-[3-(1-adamantyl)-4-methoxyphenoxymethyl]-4-thiophenecarboxylate 210 mg (7 mmol) of sodium hydride (80% in oil) and 10 ml of DMF were introduced into a three-necked flask under a stream of nitrogen. A solution of 1.8 g (7 mmol) of 3-(1-adamantyl)-4-methoxyphenol in 20 ml of DMF was added dropwise and the mixture was stirred until the evolution of gas had ceased. A solution of 1.7 g (7.2 mmol) of methyl 2-bromomethyl-4-thiophenecarboxylate in 15 ml of DMF was then added and the mixture was stirred at room temperature for two hours. The reaction medium was poured into water and extracted with ethyl ether. The organic phase was separated out after settling had taken place, dried over magnesium sulfate and evaporated. The solid obtained was triturated from hexane, filtered off and dried. 2.6 g (90%) of the expected methyl ester, having a melting point of 97°–8° C., were recovered.

(b) Synthesis of 2-[3-(1-adamantyl)-4-methoxyphenoxymethyl]-4-thiophenecarboxylic acid In a manner analogous to that of Example 14(b), from 2 g (5.6 mmol) of the above methyl ester (a), 1.7 g (88%) of 2-[3-(1-adamantyl)-4-methoxyphenoxymethyl]-4-thiophenecarboxylic acid, having a melting point of 198°–200° C., was recovered.

EXAMPLE 18

Preparation of 2-[3-(1-adamantyl)-4-methoxyphenylaminomethyl]-4-thiophenecarboxylic acid (a) Preparation of methyl 2-[3-(1-adamantyl)-4-methoxyphenylaminomethyl]-4-thiophenecarboxylate In a manner analogous to that of Example 17(a), by reaction of 2.4 g (6.8 mmol) of 3-(1-adamantyl)-4-methoxytrifluoroacetanilide were reacted with 1.6 g (6.8 mmol) of methyl 2-bromomethyl-4-thiophenecarboxylate and 2.6 g (75%) of the expected methyl ester were recovered in the form of a yellow oil.

(b) Synthesis of 2-[3-(1-adamantyl)-4-methoxyphenylaminomethyl]-4-thiophenecarboxylic acid In a manner analogous to that of Example 14(b), starting with 2.6 g (5.1 mmol) of the above methyl ester (a), 1.5 g (74%) of 2-[3-(1-adamantyl)-4-methoxyphenylaminomethyl]-4-thiophenecarboxylic acid, having a melting point of 212°–4° C., was recovered.

EXAMPLE 19

Preparation of 2-[3-(1-adamantyl)-4-methoxyphenylthiomethyl]-4-thiophenecarboxylic acid (a) Preparation of methyl 2-[3-(1-adamantyl)-4-methoxyphenylthiomethyl]-4-thiophenecarboxylate In a manner analogous to that of Example 17(a), 800 mg (2.9 mmol) of 3-(1-adamantyl)-4-methoxythiophenol were reacted with 690 mg (2.9 mmol) of methyl 2-bromomethyl-4-thiophenecarboxylate and 700 mg (56%) of the expected methyl ester were recovered in the form of a colorless oil.

(b) Synthesis of 2-[3-(1-Adamantyl)-4-methoxyphenylthiomethyl]-4-thiophenecarboxylic acid In a manner analogous to that of Example 14(b), from 700 mg (1.6 mmol) of the above methyl ester (a), 460 mg (68%) of 2-[3-(1-adamantyl)-4-methoxyphenylthiomethyl]-4-

EXAMPLE 20

Preparation of 4-[3-(1-adamantyl)-4-(2,2-dimethyl-1,3-dioxolane-4-methyloxy)benzoyloxy]benzoic acid:

(a) Preparation of allyl 4-[3-(1-adamantyl)-4-(2,2-dimethyl-1,3-dioxolane-4-methyloxy)benzoyloxy]benzoate In a manner analogous to that of Example 14(d), 4.3 g (10.7 mmol) of 3-(1-adamantyl)-4-(2,2-dimethyl-1,3-dioxolane-4-methyloxy)benzoyl chloride were reacted with 1.9 g (10.7 mmol) of allyl 4-hydroxybenzoate and 4.24 g (72%) of the expected allylic ester, having a melting point of 106°–7° C., were recovered.

(b) Synthesis of 4-[3-(1-adamantyl)-4-(2,2-dimethyl-1,3-dioxolane-4-methyloxy)benzoyloxy]benzoic acid 1 g (1.83 mmol) of the above allylic ester (a), 10 ml of THF and 104 mg of tetrakis(triphenylphosphine)palladium (0) were introduced into a three-necked flask under a stream of nitrogen. 1.6 ml (18.3 mmol) of morpholine were added dropwise and the mixture was stirred at room temperature for three hours. The reaction medium was poured into ice-water, acidified to pH 3 and extracted with ethyl ether. The organic phase was separated out after settling had taken place, dried over magnesium sulfate and evaporated. The residue obtained was purified by chromatography on a column of silica, eluted with a mixture of dichloromethane and ethyl acetate (50/50). After evaporation of the solvents, 435 mg (47%) of 4-[3-(1-adamantyl)-4-(2,2-dimethyl-1,3-dioxolane-4-methyloxy)benzoyloxy]benzoic acid, having a melting point of 238°–40° C., were recovered.

EXAMPLE 21

Preparation of 4-[3-hydroxy-3-[5-(1-adamantyl)-2,4-di(methoxyethoxymethoxy)-phenyl]-1-propynyl] benzoic acid (a) Preparation of 5-(1-adamantyl)-2,4-dihydroxybenzaldehyde 40 g (0.29 mol) of 2,4-dihydroxybenzaldehyde, 600 ml of dichloromethane and 46.4 g (0.34 mol) of 1-adamantanol were introduced into a round-bottomed flask and 24 ml of concentrated sulfuric acid were added. The reaction medium was stirred at room temperature for twelve hours and was then poured into water. The organic phase was separated out after settling had taken place, dried over magnesium sulfate and evaporated. The residue obtained was purified by chromatography on a column of silica, eluted with dichloromethane. 50.8 g (64%) of the expected aldehyde, having a melting point of 259°–61° C., were recovered.

(b) Preparation of 5-(1-adamantyl)-2,4-di(methoxyethoxymethoxy)benzaldehyde

In a manner analogous to that of Example 17(a), 25 g (91.9 mmol) of 5-(1-adamantyl)-2,4-dihydroxybenzaldehyde were reacted with 26.2 ml (0.23 mol) of 2-methoxyethoxymethyl chloride and 31 g (75%) of the expected compound were recovered in the form of a yellow oil.

(c) Preparation of a-trimethylsilylethynyl-5-(1-adamantyl)-2,4-di(methoxyethoxymethoxy)benzene-methanol:

450 μl (3.2 mmol) of trimethylsilylacetylene and 50 ml of THF were introduced into a three-necked flask. A solution of 1.3 ml (3.2 mmol) of n-butyllithium (2.5M in hexane) was added dropwise, at −78° C. and under a stream of nitrogen, and the mixture was permitted to warm to room temperature. This solution was introduced dropwise into a solution of 1.3 g (2.9 mmol) of 5-(1-adamantyl)-2,4-di(methoxyethoxymethoxy)benzaldehyde in 50 ml of THF, at −78° C. The reaction medium was permitted to warm to room temperature, poured into aqueous ammonium chloride solution and extracted with ethyl ether. The organic phase was separated out after settling had taken place, dried over magnesium sulfate and evaporated. 1.6 g (100%) of the expected alcohol was recovered in the form of a yellow oil.

(d) Preparation of a-ethynyl-5-(1-adamantyl)-2,4-di(methoxyethoxymethoxy)benzenemethanol:

1.6 g (2.9 mmol) of a-trimethylsilylethynyl-5-(1-adamantyl)-2,4-di(methoxyethoxymethoxy)benzenemethanol and 50 ml of THF were introduced into a round-bottomed flask and 3.2 ml (3.5 mmol) of tetrabutylammonium fluoride solution (1.1M in THF) were added dropwise. The reaction medium was stirred at room temperature for one hour and was then poured into water and extracted with ethyl ether. The organic phase was separated out after settling had taken place, dried over magnesium sulfate and evaporated. The residue obtained was purified by chromatography on a column of silica, eluted with a mixture of dichloromethane and ethyl ether (95/5). After evaporation of the solvents, 760 mg (55%) of expected compound were recovered in the form of a yellow oil.

(e) Preparation of methyl 4-[3-hydroxy-3-[5-(1-adamantyl)-2,4-di(methoxyethoxymethoxy)phenyl]-1-propynyl] benzoate 760 mg (1.6 mmol) of a-ethynyl-5-(1-adamantyl)-2,4-di(methoxyethoxymethoxy)benzenemethanol, 420 mg (1.6 mmol) of methyl 4-iodobenzoate and 20 ml of triethylamine were introduced into a three-necked flask. The reaction medium was degassed with nitrogen for 30 min, then 90 mg of bis(triphenylphosphine)palladium(II) chloride and 37 mg of copper iodide were added successively. The reaction medium was stirred at room temperature for four hours, then evaporated to dryness, and the residue obtained was taken up in water and ethyl ether. The organic phase was separated out after settling had taken place, dried over magnesium sulfate and evaporated. The residue obtained was purified by chromatography on a column of silica, eluted with dichloromethane and 800 mg (82%) of the expected methyl ester were recovered in the form of a brown oil.

(f) Synthesis of 4-[3-hydroxy-3-[5-1-adamantyl)-2,4-di(methoxyethoxymethoxy)-phenyl]-1-propynyl]benzoic acid:

800 mg (1.3 mmol) of the above methyl ester (e), 340 mg (7.8 mmol) of lithium hydroxide and 50 ml of THF were introduced into a round-bottomed flask and the mixture was heated at reflux for twelve hours. It was evaporated to dryness, the residue was taken up in water, acidified to pH 1 and extracted with ethyl ether. The organic phase was separated out after settling had taken place, dried over magnesium sulfate and evaporated. The residue obtained was purified by chromatography on a column of silica, eluted with ethyl ether. 420 mg (54%) of 4-[3-hydroxy-3-[3-1-adamantyl)-2,4-di(methoxyethoxymethoxy)phenyl]-1-propynyl]benzoic acid, having a melting point of 79°–81° C., were recovered.

EXAMPLE 22

Preparation of 4-[3-(1-adamantyl)-4-methoxyethoxymethoxybenzoylthio]benzoic acid 1.54 g (10 mmol) of 4-mercaptobenzoic acid and 40 ml of pyridine were introduced into a round-bottomed flask. A solution of 3.75 g (10 mmol) of 3-(1-adamantyl)-4-methoxyethoxymethoxybenzoyl chloride prepared in Example 10(c) was added dropwise and the mixture was stirred at room temperature for six hours. The mixture was evaporated to dryness, the residue was taken up in water and ethyl ether. The organic phase was separated out after settling had taken place, washed with water, dried over magnesium sulfate and evaporated. The solid obtained was recrystallized from a diisopropyl ether/methanol mixture, filtered off and dried. 2.94 g (59%) of 4-[3-(1-adamantyl)-4-methoxyethoxymethoxybenzoylthio]benzoic acid, having a melting point of 187°–8° C., were recovered.

EXAMPLE 23

Preparation of N-methyl-4-[3-(1-adamantyl)-4-methoxyethoxymethoxyphenylcarboxamido]benzoic acid (a) Preparation of allyl N-methyl-4-[3-(1-adamantyl)-4-methoxyethoxymethoxybenzamido]benzoate In a manner analogous to that of Example 16(a), 1.35 g (2.6 mmol) of allyl 4-[3-(1-adamantyl)-4-methoxyethoxymethoxybenzamido]-benzoate prepared in Example 10(d) was reacted with 190 µl (3.1 mmol) of iodomethane and 1.38 g (100%) of the expected allylic ester was recovered.

(b) Synthesis of N-methyl-4-[3-(1-adamantyl)-4-methoxyethoxymethoxyphenylcarboxamido]benzoic acid In a manner analogous to that of Example 20(b), from 1.32 g (2.5 mmol) of the above allylic ester (a), 740 mg (60%) of N-methyl-4-[3-(1-adamantyl)-4-methoxyethoxymethoxyphenylcarboxamido]benzoic acid, having a melting point of 159°–60° C., were recovered.

EXAMPLE 24

Preparation of 4-[3-(1-adamantyl)-4-methoxyethoxymethoxyphenylthiocarboxamido]benzoic acid (a) Preparation of allyl 4-[3-(1-adamantyl)-4-methoxyethoxymethoxyphenylthiocarboxamido]benzoate In a manner analogous to that of Example 6(a), 2 g (3.9 mmol) of allyl 4-[3-(1-adamantyl)-4-methoxyethoxymethoxythiocarboxamido]benzoate was reacted with 940 mg (2.3 mmol) of Lawesson's reagent and 1.93 g (92%) of the expected allylic ester was recovered.

(b) Synthesis of 4-[3-(1-adamantyl)-4-methoxyethoxymethoxnphenylthiocarboxamido]benzoic acid In a manner analogous to that of Example 20(b), from 1.9 g (3.5 mmol) of the above allylic ester(a), 50 mg (29%) of 4-[3-(1-adamantyl)-4-methoxyethoxymethoxyphenylthiocarboxamido]benzoic acid, having a melting point of 98°—9° C., were recovered.

EXAMPLE 25

Preparation of (E)-4-[[3-oxo-3-[3-(1-adamantyl)-4-methoxymethoxyphenyl]-1-propenyl]]benzoic acid (a) Preparation of methyl 3-(1-adamantyl)-4-methoxymethoxybenzoate 9 g (0.3 mol) of sodium hydride (80% in oil) and 50 ml of DMF were introduced into a three-necked flask under a stream of nitrogen. A solution of 71.6 g (0.25 mol) of methyl 3-(1-adamantyl)-4-hydroxybenzoate in 500 ml of DMF was added dropwise and the mixture was stirred until the evolution of gas had ceased. 22.8 ml (0.3 mol) of methoxymethyl chloride were then added and the mixture was stirred at room temperature for one hour. The reaction medium was poured into water and extracted with ethyl ether. The organic phase was separated out after settling had taken place, dried over magnesium sulfate and evaporated. 67.7 g (82%) of the expected compound were recovered in the form of an oil.

(b) Preparation of 3-(1-adamantyl)-4-methoxymethoxybenzoic acid

In a manner analogous to that of Example 14(b), from 67.7 g (0.2 mol) of the above methyl ester (a), 59 g (91%) of 3-(1-adamantyl)-4-methoxymethoxybenzoic acid were recovered.

(c) Preparation of 3-(1-adamantyl)-4-methoxymethoxyacetophenone 58 g (0.183 mol) of 3-(1-adamantyl)-4-methoxymethoxybenzoic acid and 500 ml of anhydrous ethyl ether were introduced into a three-necked flask under a stream of nitrogen. 252 ml (0.4 mol) of methyllithium (1.6M in ether) were added dropwise, at −20° C., and the mixture was then stirred for three hours at room temperature. The reaction medium was poured into saturated aqueous ammonium chloride solution and the organic phase was separated out after settling had taken place, dried over magnesium sulfate and evaporated. 59.6 g (100%) of the expected acetophenone were recovered in the form of a pale yellow oil.

(d) Preparation of methyl (E)-4-[[3-oxo-3-[3-(1-adamantyl)-4-methoxymethoxyphenyl]-1-propenyl]] benzoate 40.9 g (0.13 mol) of 3-(1-adamantyl)-4-methoxymethoxyacetophenone, 23.47 g (0.143 mol) of methyl 4-formylbenzoate and 600 ml of methanol were introduced into a round-bottomed flask. 24.8 ml (0.13 mol) of sodium methoxide solution (5.25M) were added and the mixture was stirred at room temperature for 18 hours. The mixture was evaporated to dryness and the residue was taken up in a water/ethyl acetate mixture. The organic phase was separated out after settling had taken place, dried over magnesium sulfate and evaporated. The residue obtained was purified by trituration from a mixture of hexane and ethyl acetate, filtered and dried. 46.1 g (77%) of methyl (E)-4-[[3-oxo-3-[3-(1-adamantyl)-4-methoxymethoxyphenyl]-1-propenyl]]benzoate, having a melting point of 170°—1° C., were recovered.

(e) Synthesis of (E)-4-[[3-oxo-3-[3-(1-adamantyl)-4-methoxymethoxyphenyl]-1-propenyl]]benzoic acid In a manner analogous to that of Example 2(a), from 5 g (10.8 mmol) of methyl (E)-4-[[3-oxo-3-[3-(1-adamantyl)-4-methoxymethoxyphenyl]-1-propenyl]]benzoate, 3 g (62%) of the expected acid, having a melting point of 205°—6° C., were recovered.

EXAMPLE 26

Preparation of (E)-4-[[3-oxo-3-[3-(1-adamantyl)-4-hydroxyphenyl]-1-propenyl]]benzoic acid (a) Preparation of methyl (E)-4-[[3-oxo-3-(3-(1-adamantyl)-4-hydroxyphenyl]-1-propenyl]]benzoate 40.2 g (87.4 mmol) of methyl (E)-4-[[3-oxo-3-(1-adamantyl)-4-methoxymethoxyphenyl]-1-propenyl]] benzoate, one liter of methanol and 300 ml of THF were introduced into a round-bottomed flask. 50 ml of concentrated sulfuric acid were added and the mixture was heated at reflux for four hours. The reaction medium was evaporated and the residue was taken up in an ethyl acetate/water mixture. The organic phase was separated out after settling had taken place, dried over magnesium sulfate and evaporated. The solid obtained was triturated from an ethyl acetate/hexane mixture (30/70), filtered off and dried. 32.1 g (88%) of the expected methyl ester, having a melting point of 256°—7° C., were recovered.

(b) Synthesis of (E)-4-[[3-oxo-3-[3-(1-adamantyl)-4-hydroxphenyl]-1-propenyl]]benzoic acid In a manner analogous to that of Example 2(a), from 5 g (12 mmol) of the above methyl ester, 4.8 g (100%) of (E)-4-[[3-oxo-3-[3-(1-adamantyl)-4-hydroxyphenyl]-1-propenyl]]benzoic acid, having a melting point >300° C. with decomposition, were recovered.

EXAMPLE 27

In this example, various specific formulations based on the compounds according to the invention are illustrated.

(A) ORAL ROUTE:

(a) 0.2 g Tablets:

| | | |
|---|---|---|
| (i) | Compound of Example 1 | 0.001 g |
| (ii) | Starch | 0.114 g |
| (iii) | Dicalcium phosphate | 0.020 g |
| (iv) | Silica | 0.020 g |
| (v) | Lactose | 0.030 g |
| (vi) | Talc | 0.010 g |
| (vii) | Magnesium stearate | 0.005 g |

(b) Drinkable suspension in 5 ml ampules:

| | | |
|---|---|---|
| (i) | Compound of Example 2 | 0.001 g |
| (ii) | Glycerol | 0.500 g |
| (iii) | 70% Sorbitol | 0.500 g |
| (iv) | Sodium saccharinate | 0.010 g |
| (v) | Methyl para-hydroxybenzoate | 0.040 g |
| (vi) | Flavoring qs | |
| (viii) | Purified water qs | 5 ml |

(c) 0.8 g Tablets:

| | | |
|---|---|---|
| (i) | Compound of Example 6 | 0.500 g |
| (ii) | Pregelatinized starch | 0.100 g |
| (iii) | Microcrystalline cellulose | 0.115 g |
| (iv) | Lactose | 0.075 g |
| (v) | Magnesium stearate | 0.010 g |

(d) Drinkable suspension in 10 ml ampules:

| | | |
|---|---|---|
| (i) | Compound of Example 4 | 0.05 g |
| (ii) | Glycerol | 1.000 g |
| (iii) | 70% Sorbitol | 1.000 g |
| (iv) | Sodium saccharinate | 0.010 g |
| (v) | Methyl para-hydroxybenzoate | 0.080 g |
| (vi) | Flavoring qs | |
| (vii) | Purified water qs | 10 ml |

(B) TOPICAL ROUTE:

(a) Ointment:

| | | |
|---|---|---|
| (i) | Compound of Example 1 | 0.020 g |
| (ii) | Isopropyl myristate | 81.700 g |
| (iii) | Fluid liquid petrolatum | 9.100 g |
| (iv) | Silica ("Aerosil 200" marketed by Degussa) | 9.180 g |

(b) Ointment:

| | | |
|---|---|---|
| (i) | Compound of Example 6 | 0.300 g |
| (ii) | White petrolatum codex | 100 g |

(c) Nonionic water-in-oil cream:

| | | |
|---|---|---|
| (i) | Compound of Example 1 | 0.100 g |
| (ii) | Mixture of emulsifying lanolin alcohols, waxes and oils ("anhydrous eucerin") marketed by BDF) | 39.900 g |
| (iii) | Methyl para-hydroxybenzoate | 0.075 g |
| (iv) | Propyl para-hydroxybenzoate | 0.075 g |
| (v) | Sterile demineralized water qs | 100 g |

(d) Lotion:

| | | |
|---|---|---|
| (i) | Compound of Example 1 | 0.100 g |
| (ii) | Polyethylene glycol (PEG 400) | 69.900 g |
| (iii) | 95% Ethanol | 30.000 g |

(e) Hydrophobic ointment:

| | | |
|---|---|---|
| (i) | Compound of Example 2 | 0.300 g |
| (ii) | Isopropyl myristate | 36.400 g |
| (iii) | Silicone oil ("Rhodorsil 47 V 300" marketed by Rhône-Poulenc) | 36.400 g |
| (iv) | Beeswax | 13.600 g |
| (v) | Silicone oil ("Abil 300,000 cst" marketed by Goldschmidt) | 100 g |

(f) Nonionic oil-in-water cream:

| | | |
|---|---|---|
| (i) | Compound of Example 4 | 0.500 g |
| (ii) | Cetyl alcohol | 4.000 g |
| (iii) | Glyceryl monostearate | 2.500 g |
| (iv) | PEG 50 stearate | 2.500 g |
| (v) | Karite butter | 9.200 g |
| (vi) | Propylene glycol | 2.000 g |
| (vii) | Methyl para-hydroxybenzoate | 0.075 g |
| (viii) | Propyl para-hydroxybenzoate | 0.075 g |
| (ix) | Sterile demineralized water | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An adamantyl-substituted biaromatic compound having the structural formula (I):

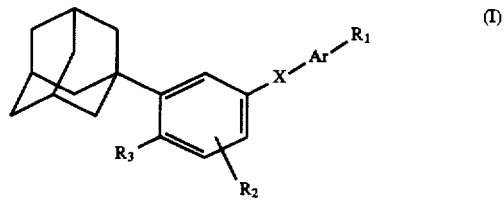

in which $R_1$ is a —$CH_3$ radical, a —$(CH_2)_n$—O—$R_4$ radical, an —O—$(CH_2)_m$—(CO)n—$R_5$ radical, a —CO—$R_6$ radical, or a —CO—O—$R_7$ radical, wherein values of m and n and the radicals $R_4$ to $R_7$ are as defined below; $R_2$ is a hydrogen atom, a halogen atom, a linear or branched alkyl radical having from 1 to 20 carbon atoms, an —$OR_4$ radical, or an —O—$CH_2$—O—$CH_2$—$CH_2$—O—$CH_3$ radical; $R_3$ is a —Y—$(CH_2)_p$—Y—$(CH_2)_q$—$R_8$ radical, a —$(CH_2)_p$—Y—$(CH_2)_q$—$R_8$ radical, a —Y—$(CH_2)_q$—$R_8$ radical, a —CH=CH—$(CH_2)_r$—$R_8$ radical, or a —$(CH_2)_q$—$R_8$ radical, wherein the values of p, q and r and the radicals Y and $R_8$ are as defined below; X is a bridging radical selected from among those of the following formulae (a)–(k), which may be oriented left-to-right or right-to-left:

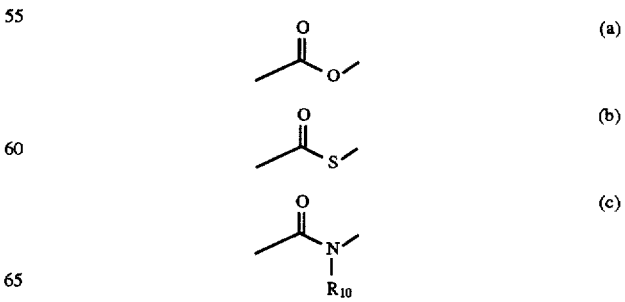

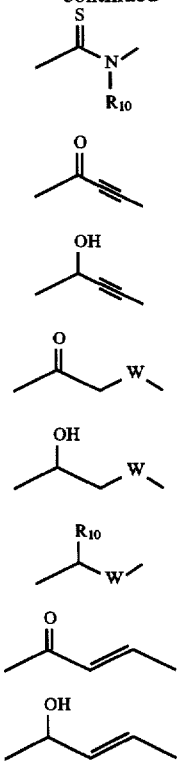

Ar is a radical selected from among those of the following formulae (a')–(f'):

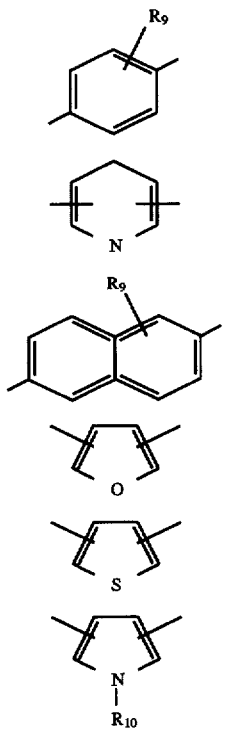

m is an integer equal to 1, 2 or 3; n is an integer equal to 0 or 1; p is an integer ranging from 1 to 12, inclusive; q is an integer ranging from 0 to 12, inclusive; r is an integer ranging from 0 to 10, inclusive; t is an integer equal to 0, 1 or 2; Y is an oxygen atom or a radical S(O)t; W is an oxygen atom, a radical S(O)t or a radical N—$R_{10}$; $R_4$ is a hydrogen atom, a lower alkyl radical or a radical —CO—$R_{11}$; $R_5$ is a lower alkyl radical or a heterocycle; $R_6$ is a hydrogen atom, a lower alkyl radical, or a radical

in which R' and R", which may be identical or different, are each a hydrogen atom, a lower alkyl radical, a mono- or polyhydroxyalkyl radical, an optionally substituted aryl radical, or an amino acid or peptide or sugar residue, with the proviso that R' and R" may together form, with the nitrogen atom from which they depend, a nitrogen-containing heterocycle; $R_7$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; $R_8$ is a hydrogen atom, a branched alkyl radical having from 1 to 20 carbon atoms, a C3–C6 cycloaliphatic radical, a monohydroxyalkyl radical or a polyhydroxyalkyl radical, said hydroxyls optionally being protected as methoxy, acetoxy or acetonide groups, an aryl radical, an alkynyl radical, a —CO—$R_6$ radical, a —CO—O—$R_7$ radical, an amino alkyl radical whose amine function is optionally substituted with one or two lower alkyl radicals, or a heterocycle, wherein $R_7$ is as defined above; $R_9$ is a hydrogen or halogen atom, a linear or branched alkyl radical having from 1 to 20 carbon atoms, an —$OR_4$ radical or an —O—$CH_2$—O—$CH_2$—$CH_2$—O—$CH_3$ radical; the radicals $R_{10}$, which may be identical or different, are each a hydrogen atom or a lower alkyl radical; and $R_{11}$ is a lower alkyl radical, with the provisos that (1) when X is a bridging radical of formula (a), (b), (c), (g), (h), (j) or (k), then $R_3$ is other than a radical —Y—$(CH_2)_q$—$R_8$, —CH═CH—$(CH_2)_r$—$R_8$ or —$(CH_2)_q$—$R_8$ in which $R_8$ is a hydrogen atom, (2) when X is a bridging radical of formula (a), then $R_3$ is other than the radical —Y—$(CH_2)_q$—$R_8$, (3) when X is a bridging radical of formula (b) and $R_3$ is the radical —Y—$(CH_2)_q$—$R_8$ in which Y is a sulfur atom, then R8 is other than an aryl radical, and (4) when X is a bridging radical of formula (g), (h), (j) or (k) and $R_3$ is a radical —$(CH_2)_q$—$R_8$ then $R_8$ is other than a monohydroxyalkyl or polyhydroxyalkyl radical; or a pharmaceutically/cosmetically acceptable derivative or optical or geometric isomer thereof.

2. The adamantyl-substituted biaromatic compound as defined by claim 1, wherein formula (I), Ar has the structure (a').

3. The adamantyl-substituted biaromatic compound as defined by claim 1, wherein formula (I), Ar has the structure (b').

4. The adamantyl-substituted biaromatic compound as defined by claim 1, wherein formula (I), Ar has the structure (c').

5. The adamantyl-substituted biaromatic compound as defined by claim 1, wherein formula (I), Ar has the structure (d').

6. The adamantyl-substituted biaromatic compound as defined by claim 1, wherein formula (I), Ar has the structure (e').

7. The adamantyl-substituted biaromatic compound as defined by claim 1, wherein formula (I), Ar has the structure (f').

8. The adamantyl-substituted biaromatic compound as defined by claim 1, wherein formula (I), X has the structure (a).

9. The adamantyl-substituted biaromatic compound as defined by claim 1, wherein formula (I), X has the structure (b).

10. The adamantyl-substituted biaromatic compound as defined by claim 1, wherein formula (I), X has the structure (c).

11. The adamantyl-substituted biaromatic compound as defined by claim 1, wherein formula (I), X has the structure (d).

12. The adamantyl-substituted biaromatic compound as defined by claim 1, wherein formula (I), X has the structure (e).

13. The adamantyl-substituted biaromatic compound as defined by claim 1, wherein formula (I), X has the structure (f).

14. The adamantyl-substituted biaromatic compound as defined by claim 1, wherein formula (I), X has the structure (g).

15. The adamantyl-substituted biaromatic compound as defined by claim 1, wherein formula (I), X has the structure (h).

16. The adamantyl-substituted biaromatic compound as defined by claim 1, wherein formula (I), X has the structure (i).

17. The adamantyl-substituted biaromatic compound as defined by claim 1, wherein formula (I), X has the structure (j).

18. The adamantyl-substituted biaromatic compound as defined by claim 1, wherein formula (I), X has the structure (k).

19. The adamantyl-substituted biaromatic compound as defined by claim 1, comprising a pharmaceutically acceptable salt thereof.

20. The adamantyl-substituted biaromatic compound as defined by claim 1, comprising at least one lower alkyl radical substituent selected from among methyl, ethyl, isopropyl, butyl, tert-butyl, hexyl, nonyl and dodecyl radicals.

21. The adamantyl-substituted biaromatic compound as defined by claim 1, comprising at least one linear alkyl radical substituent selected from among methyl, ethyl, propyl, 2-ethylhexyl, octyl, dodecyl, hexadecyl and octadecyl radicals.

22. The adamantyl-substituted biaromatic compound as defined by claim 1, comprising at least one branched alkyl radical substituent selected from among 2-methylbutyl, 2-methylpentyl, 1-methylhexyl and 3-methylheptyl radicals.

23. The adamantyl-substituted biaromatic compound as defined by claim 1, comprising at least one monohydroxyalkyl radical substituent selected from among 2-hydroxyethyl, 2-hydroxypropyl and 3-hydroxypropyl radicals.

24. The adamantyl-substituted biaromatic compound as defined by claim 1, comprising at least one polyhydroxyalkyl radical substituent selected from among 2,3-dihydroxypropyl, 2,3,4-trihydroxybutyl and 2,3,4,5-tetrahydroxypentyl radicals, and the pentaerythritol residue.

25. The adamantyl-substituted biaromatic compound as defined by claim 1, comprising at least one aryl radical substituent selected from among phenyl radicals optionally substituted by at least one halogen atom, or at least one hydroxyl or nitro functional group.

26. The adamantyl-substituted biaromatic compound as defined by claim 1, comprising at least one aralkyl radical substituent selected from among benzyl or phenethyl radicals optionally substituted by at least one halogen atom, or at least one hydroxyl or nitro functional group.

27. The adamantyl-substituted biaromatic compound as defined by claim 1, comprising at least one alkenyl radical substituent selected from among those having from 2 to 5 carbon atoms and one or more sites of ethylenic unsaturation.

28. The adamantyl-substituted biaromatic compound as defined by claim 1, comprising at least one sugar residue substituent derived from glucose, galactose, mannose or glucuronic acid.

29. The adamantyl-substituted biaromatic compound as defined by claim 1, comprising at least one amino acid residue substituent derived from lysine, glycine or aspartic acid.

30. The adamantyl-substituted biaromatic compound as defined by claim 1, comprising at least one dipeptide or tripeptide residue substituent.

31. The adamantyl-substituted biaromatic compound as defined by claim 1, comprising at least one heterocyclic radical substituent selected from among piperidino, morpholino, pyrrolidino and piperazino radicals, optionally substituted in the 4-position by a $C_1$—$C_6$ alkyl or mono- or polyhydroxyalkyl radical.

32. The adamantyl-substituted biaromatic compound as defined by claim 1, comprising at least one amino alkyl radical substituent having from 1 to 6 carbon atoms.

33. The adamantyl-substituted biaromatic compound as defined by claim 1, comprising at least one alkynyl radical substituent having from 2 to 6 carbon atoms.

34. The adamantyl-substituted biaromatic compound as defined by claim 1, comprising at least one cycloaliphatic radical substituent having from 3 to 6 carbon atoms.

35. The adamantyl-substituted biaromatic compound as defined by claim 1, comprising at least one halogen atom substituent selected from among fluorine, chlorine and bromine atoms.

36. The adamantyl-substituted biaromatic compound as defined by claim 19, comprising an alkali or alkaline earth metal, zinc or amine salt.

37. The adamantyl-substituted biaromatic compound as defined by claim 1, selected from among 4-[3-(1-adamantyl)-4-methoxyphenylthiomethyl]benzoic acid; 4-[3-(1-adamantyl)-4-methoxyphenylsulfinylmethyl]benzoic acid; 4-[3-(1-adamantyl)-4-methoxyphenylmethylsulfonyl]benzoic acid; 4-[3-(1-adamantyl)-4-methoxyphenylmethylsulfinyl]benzoic acid; 4-[3-(1-adamantyl)-4-methoxyphenylsulfonylmethyl]benzoic acid; 4-[3-(1-adamantyl)-4-methoxyphenylthiocarboxamido]benzoic acid; 4-[3-(1-adamantyl)-4-methoxyphenylmethylthio]benzoic acid; 4-[3-(1-adamantyl)-4-methoxyphenylmethylamino]benzoic acid; 4-[[3-oxo-3 [3-(1-adamantyl)-4-methoxyphenyl]-1-propynyl]]benzoic acid; 4-[3-(1-adamantyl)-4-methoxyethoxymethoxybenzamido]benzoic acid; 4-[3-(1-adamantyl)-4-methoxyethoxymethoxybenzoyloxy]benzoic acid; (E)-4-[[3-oxo-3-[3-(1-adamantyl)-4-methoxyethoxymethoxyphenyl]-1-propenyl]]benzoic acid; 4-[[3-hydroxy-3-[3-(1-adamantyl)-4-methoxyethoxymethoxyphenyl]-1-propynyl]]benzoic acid; 4-[3-(1-adamantyl)-4-(2,2-dimethyl-1,3-dioxolane-4-methyloxy)phenylcarboxamido]benzoic acid; 4-[3-(1-adamantyl)-4-(2,3-dihydroxypropyloxy)phenylcarboxamido]benzoic acid; 4-[3-(1-adamantyl)-4-methoxycarbonylmethyloxyphenylcarboxamido]benzoic acid; 2-[3-(1-adamantyl)-4-methoxyphenoxymethyl]-4-thiophenecarboxylic acid; 2-[3-(1-adamantyl)-4-methoxyphenylaminomethyl]-4-thiophenecarboxylic acid; 2-[3-(1-adamantyl)-4-methoxyphenylthiomethyl]-4- thiophenecarboxylic acid; 4-[3-(1-adamantyl)-4-(2,2-dimethyl-1,3-dioxolane-4-methyloxy)benzoyloxy]benzoic acid; 4-[3-hydroxy-3-[5-(1-adamantyl)-2,4-dimethoxyethoxymethoxyphenyl]-1-propynyl]benzoic acid; 4-[3-(1-adamantyl)-4-methoxyethoxymethoxybenzoylthio] benzoic acid; N-Methyl-4-[3-(1-adamantyl)-4-methoxyethoxymethoxyphenylcarboxamido]benzoic acid; 4-[3-(1-adamantyl)-4-methoxyethoxymethoxyphenylthiocarboxamido]benzoic acid; (E)-4-[[3-oxo-3-[3-(1-adamantyl)-4-methoxymethoxyphenyl]-1-propenyl]]benzoic acid; (E)-4-[[3-oxo-3-[3-(1-adamantyl)-4-hydroxyphenyl]-1-propenyl]] benzoic acid; (E)-4-[[3-oxo-3-[3-(1-adamantyl)-4-methoxyphenyl]-1-propenyl]]benzoic acid; (E)-4-[[3-oxo-3-[3-(1-adamantyl)-4-(3-hydroxypropyloxy)phenyl]-1-propenyl]]benzoic acid; 4-[3-(1-adamantyl)-4-methoxyethoxymethoxybenzoyloxy]benzaldehyde; 4-[3-(1-adamantyl)-4-methoxyethoxymethoxybenzoyloxy] benzenemethanol; (E)-N-ethyl-4-[[3-oxo-3-[3-(1-adamantyl)-4-methoxyethoxymethoxyphenyl]-1-propenyl]] benzamide; (E)-N-(4-hydroxyphenyl)-4-[[3-oxo-3-[3-(1-adamantyl)-4-methoxyethoxymethoxyphenyl]-1-propenyl]] benzamide; (E)-4-[[3-oxo-3-[3-(1-adamantyl)-4-methoxyethoxymethoxyphenyl]-1-propenyl]]phenol.

38. The adamantyl-substituted biaromatic compound as defined by claim 1, wherein formula (I), at least one of the following conditions exist:

$R_1$ is the radical —COO—$R_7$ or —CO—$R_6$;

$R_3$ is the radical —Y—$(CH_2)_p$—Y—$(CH_2)_q$—$R_8$, —$(CH_2)_p$—Y—$(CH_2)_q$—$R_8$ or —Y—$(CH_2)_q$—$R_8$;

X is a bridging radical of formula (a), (e), (f), (j) or (k); and

Ar is a radical of formula (a') or (b').

39. A pharmaceutical composition of matter, comprising a therapeutically effective amount of an adamantyl-substituted biaromatic compound as defined by claim 1, or pharmaceutically acceptable derivative or isomer thereof, and a pharmaceutically acceptable vehicle, carrier or diluent therefor.

40. The pharmaceutical composition as defined by claim 39, further comprising a retinoid compound, a D vitamin or derivative thereof, a corticosteroid, an anti-free radical agent, an α-hydroxy or α-keto acid or derivative thereof, an ion channel blocker, or combination thereof.

41. The pharmaceutical composition as defined by claim 39, comprising a tablet, a capsule, a syrup, a dragee, a suspension, an elixir, a solution, a powder, granules, an emulsion, microspheres, nanospheres, lipid vesicles, polymeric vesicles, or an injectable.

42. The pharmaceutical composition as defined by claim 39, comprising an ointment, a cream, a milk, a salve, an impregnated pad, a gel, a spray, or a lotion.

43. The pharmaceutical composition as defined by claim 39, adopted for topical administration.

44. The pharmaceutical composition as defined by claim 39, adopted for systemic administration.

45. The pharmaceutical composition as defined by claim 39, comprising from 0.001% to 5% by weight of said adamantyl-substituted biaromatic compound, or derivative or isomer thereof.

46. A method of treating a dermatological, rheumatic, respiratory, cardiovascular, bone or ophthalmologic disorder in a mammalian organism in need of such treatment, comprising administering to such organism a therapeutically effective amount of the pharmaceutical composition as defined by claim 39.

47. A method for treating osteoporosis in a mammalian organism in need of such treatment, comprising administering to such organism a therapeutically effective amount of the pharmaceutical composition as defined by claim 39.

48. The method as defined by claim 46, comprising administering to such organism a daily dose of said adamantyl-substituted biaromatic compound of about 0.01 mg/kg to 100 mg/kg of body weight thereof.

49. A cosmetic composition of matter, comprising a cosmetically effective amount of an adamantyl-substituted biaromatic compound as defined by claim 1, or cosmetically acceptable derivative or isomer thereof, and a cosmetically acceptable vehicle, carrier or diluent therefor.

50. The cosmetic composition as defined by claim 49, comprising a cream, a milk, a lotion, a gel, an ointment, microspheres, nanospheres, lipid vesicles, polymeric vesicles, a soap, or a shampoo.

51. The cosmetic composition as defined by claim 49, comprising from 0.001% to 3% by weight of said adamantyl-substituted biaromatic compound, or derivative or isomer thereof.

52. The cosmetic composition as defined by claim 49, further comprising a retinoid compound, a D vitamin or derivative thereof, a corticosteroid, an anti-free radical agent, an α-hydroxy or α-keto acid or derivative thereof, an ion channel blocker, or combination thereof.

53. The pharmaceutical composition as defined by claim 49, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,5,11,14-eicosatetraynoic or 5,8,11-eicosatrynoic acid or ester or amide thereof, or combination thereof.

54. The pharmaceutical composition as defined by claim 49, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

55. The cosmetic composition by claim 49, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

56. The cosmetic composition as defined by claim 49, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *